United States Patent
Cazares Delgadillo et al.

(10) Patent No.: US 11,504,348 B2
(45) Date of Patent: Nov. 22, 2022

(54) IONTOPHORESIS METHOD OF DELIVERING VITAMIN C THROUGH THE SKIN AND IONTOPHORESIS DEVICE COMPRISING: AN ELECTRODE ASSEMBLY INCLUDING AT LEAST ONE ELECTRODE AND AN AQUEOUS ACTIVE AGENT

(71) Applicant: L'OREAL, Paris (FR)

(72) Inventors: Jennyfer Cazares Delgadillo, Chevilly la Rue (FR); Thi Hong Lien Planard-Luong, Chevilly la Rue (FR)

(73) Assignee: L'OREAL, Paris (FR)

( * ) Notice: Subject to any disclaimer, the term of this patent is extended or adjusted under 35 U.S.C. 154(b) by 751 days.

(21) Appl. No.: 16/062,167

(22) PCT Filed: Dec. 6, 2016

(86) PCT No.: PCT/EP2016/079870
§ 371 (c)(1),
(2) Date: Jun. 14, 2018

(87) PCT Pub. No.: WO2017/102430
PCT Pub. Date: Jun. 22, 2017

(65) Prior Publication Data
US 2018/0344681 A1 Dec. 6, 2018

(30) Foreign Application Priority Data

Dec. 15, 2015 (EP) ..................................... 15200258
Dec. 15, 2015 (EP) ..................................... 15200262

(Continued)

(51) Int. Cl.
*A61N 1/32* (2006.01)
*A61N 1/30* (2006.01)
(Continued)

(52) U.S. Cl.
CPC ............ *A61K 31/341* (2013.01); *A61K 8/676* (2013.01); *A61K 9/0014* (2013.01); *A61N 1/08* (2013.01);
(Continued)

(58) Field of Classification Search
CPC ........ A61N 1/325; A61N 1/30; A61N 1/0428; A61M 2037/0007; A61M 1/0448
See application file for complete search history.

(56) References Cited

U.S. PATENT DOCUMENTS 4,764,164 A * 8/1988 Sasaki .................... A61N 1/044
604/20
2002/0010414 A1 * 1/2002 Coston ................... A61N 1/325
604/20
(Continued)

FOREIGN PATENT DOCUMENTS

EP          1 133 985 A1    9/2001
KR    10-2005-0088878 A     9/2005
(Continued)

OTHER PUBLICATIONS

Combined Chinese Office Action and Search Report dated Nov. 4, 2020 in corresponding Chinese Patent Application No. 201680081888.3 (with English Translation of Category of Cited Documents), 8 pages.

(Continued)

*Primary Examiner* — Phillip A Gray
(74) *Attorney, Agent, or Firm* — Oblon, McClelland, Maier & Neustadt, L.L.P.

(57) ABSTRACT

A iontophoresis method (700) is described for delivering vitamin C through the skin of a biological subject, the method comprising applying (702) a selected current profile, either continuous direct current or pulsed current or a combination of both to a biological subject. A iontophoresis (Continued)

composition is further described, comprising one or more of vitamin C, vitamin C derivatives, ions of vitamin C and ions of vitamin C derivatives and further comprising a silicon material and water. A iontophoresis kit for carrying out the iontophoresis method is also disclosed. The application further describes a iontophoresis device comprising an electrode assembly and circuitry configured to concurrently generate a continuous direct current stimulus and a pulsed current stimulus; a corresponding iontophoresis method for delivering a cosmetic composition to a biological subject is also disclosed.

8 Claims, 6 Drawing Sheets

(30) Foreign Application Priority Data

May 27, 2016 (EP) ..................................... 16171763
May 27, 2016 (EP) ..................................... 16171768

(51) Int. Cl.
- *A61K 31/341* (2006.01)
- *A61K 8/67* (2006.01)
- *A61Q 19/00* (2006.01)
- *A61K 9/00* (2006.01)
- *A61N 1/08* (2006.01)

(52) U.S. Cl.
CPC ............... *A61N 1/30* (2013.01); *A61N 1/303* (2013.01); *A61N 1/325* (2013.01); *A61Q 19/00* (2013.01); *A61K 2800/83* (2013.01)

(56) References Cited

U.S. PATENT DOCUMENTS

| | | | |
|---|---|---|---|
| 2004/0071765 A1* | 4/2004 | Adachi | A61K 47/32 424/443 |
| 2005/0015042 A1 | 1/2005 | Sun et al. | |
| 2005/0019356 A1* | 1/2005 | Bissett | A61K 8/4913 424/401 |
| 2005/0049642 A1* | 3/2005 | Bernabei | A61H 39/002 607/3 |
| 2005/0177092 A1 | 8/2005 | Adachi et al. | |
| 2006/0110439 A1 | 5/2006 | Tobia et al. | |
| 2014/0276247 A1* | 9/2014 | Hall | A61N 1/3603 601/2 |
| 2014/0276248 A1 | 9/2014 | Hall et al. | |

FOREIGN PATENT DOCUMENTS

| | | |
|---|---|---|
| KR | 10-2015-0135335 A | 12/2015 |
| WO | WO 2004/047915 A1 | 6/2004 |
| WO | WO 2006/120726 A1 | 11/2006 |
| WO | WO 2014/144923 A1 | 9/2014 |
| WO | WO 2015/091044 A1 | 6/2015 |

OTHER PUBLICATIONS

Office Action dated Oct. 7, 2019 in Japanese Patent Application No. 2018-531083, 9 pages (with unedited computer generated English translation).

International Search Report dated Apr. 21, 2017 in PCT/EP2016/079870 filed Dec. 6, 2016.

Japanese Office Action dated Jun. 3, 2019 in Japanese Patent Application No. 2018-531083 (with English translation), 14 pages.

* cited by examiner

IONTOPHORESIS METHOD OF DELIVERING VITAMIN C THROUGH THE SKIN AND IONTOPHORESIS DEVICE COMPRISING: AN ELECTRODE ASSEMBLY INCLUDING AT LEAST ONE ELECTRODE AND AN AQUEOUS ACTIVE AGENT

SUMMARY

Iontophoresis Method of Delivering Vitamin C Through the Skin

In some embodiments, a method of delivering vitamin C, for example an aqueous vitamin C composition, through the skin, comprises applying a selected current profile, either continuous direct current, pulsed current or a combination of both, from any device and/or support comprising at least one electrode to a biological subject, the continuous direct current, the pulsed current or the combination of both of a character and for a duration sufficient to transdermally deliver vitamin C, for example an aqueous composition, to a biological subject, and transporting different rates of vitamin C across the skin in accordance to the selected current mode.

In some embodiments of the iontophoresis method, applying a selected current profile to a biological subject includes generating a continuous direct current stimulus having an average current density ranging from 0.001 $mA/cm^2$ to 0.5 $mA/cm^2$, in particular from 0.01 $mA/cm^2$ to 0.5 $mA/cm^2$.

In some embodiments of the iontophoresis method, applying a selected current profile to a biological subject includes generating a continuous direct current stimulus having an average current density of 0.2 $mA/cm^2$.

In some embodiments of the iontophoresis method, applying a selected current profile to a biological subject includes generating a pulsed current having sinusoidal waveforms, non-sinusoidal waveforms, or combinations thereof.

In some embodiments of the iontophoresis method, applying a selected current profile to a biological subject includes generating a pulsed current having periodic square waveforms, rectangular waveforms, saw tooth waveforms, spiked waveforms, trapezoidal waveforms, triangle waveforms, or combinations thereof.

In some embodiments of the iontophoresis method, applying a selected current profile to a biological subject includes concurrently delivering the continuous direct current and the pulsed current and generating a pulsed current stimulus having an average current density ranging from 0.005 $mA/cm^2$ to 0.5 $mA/cm^2$, in particular from 0.05 $mA/cm^2$ to 0.5 $mA/cm^2$; a pulse duration ranging from 100 microseconds to 500 microseconds, in particular from 200 microseconds to 300 microseconds; and a pulse frequency ranging from 1 Hertz to 500 Hertz, in particular from 100 Hertz to 300 Hertz.

In some embodiments of the iontophoresis method, the method further comprises transdermally delivering a composition, for example an aqueous composition, including, one or more of vitamin C, vitamin C derivatives, ions of vitamin C, and ions of vitamin C derivatives present in amounts ranging from 0.1% to 20% by weight; one or more silicon surface-active agents present in amounts ranging from 0.01% to 30% by weight; one or more ionic polymers present in amounts ranging from 0.01% to 10% by weight; and water present in an amount of at least 30% by weight.

In some embodiments of the iontophoresis method, the method further comprises:
transdermally delivering a composition including,
one or more of vitamin C, vitamin C derivatives, ions of vitamin C, and ions of vitamin C derivatives present in amounts ranging from 0.01% to 100% by weight preferably from 0.5% to 60% by weight.

In some embodiments of the iontophoresis method, the method further comprises
transdermally delivering an aqueous composition including,
one or more silicon surface-active agents present in amounts ranging from 0.01% to 30% by weight;
one or more ionic polymers present in amounts ranging from 0.01% to 10% by weight; and
water present in an amount of at least 30% by weight.

In some embodiments of the iontophoresis method, the method further comprises transdermally delivering an aqueous composition including, one or more of vitamin C, vitamin C derivatives, ions of vitamin C, and ions of vitamin C derivatives present in amounts ranging from 0.01% to 30% by weight; one or more silicon surface-active agents present in amounts ranging from 0.01% to 30% by weight; one or more non-ionic polymers present in amounts ranging from 0.01% to 20% by weight; and water present in an amount of at least 30% by weight.

In some embodiments of the iontophoresis method, transdermally delivering vitamin C, in particular the aqueous active agent composition includes, generating a continuous direct current stimulus having an average current density ranging from 0.01 $mA/cm^2$ to 0.5 $mA/cm^2$; and generating a pulsed current stimulus having an average current density ranging from 0.01 $mA/cm^2$ to 10 $mA/cm^2$; a pulse duration ranging from 10 microseconds to 500 microseconds; and a pulse frequency ranging from 10 Hertz to 500 Hertz; the continuous direct current and the pulsed current of a duration sufficient to transdermally deliver an aqueous active agent composition to a biological subject.

In some embodiments of the iontophoresis method, the method comprises a step of measuring at least one of the temperature of the skin, the impedance of the skin, and a pH of the composition.

In some embodiments of the iontophoresis method, the application of current profile is reduced to a safety level when a measured value measured by one of the sensors exceeds a safety range or a safety value.

In some embodiments of the iontophoresis method, the method comprises a step of measuring the pH of the composition. When the measured pH exceeds a pH safety range, the application of current profile is switched to a safety level, for example a safety level less than 1V, such as 0.5V. The pH safety range may be pH 4 to 7. In some embodiment, when the measured pH exceeds a pH safety range, for example the range from 4 to 7, the device switches the polarity during a short time to enable to reequilibrate the pH.

In some embodiments of the iontophoresis method, the method comprises a step of measuring the impedance of the skin. When the measured impedance exceeds an impedance safety range, the application of current profile is reduced to a safety level to avoid adverse event. The safety level may be less than 1V, such as 0.5V. The impedance safety range may be 50Ω to 1 MΩ.

In some embodiments of the iontophoresis method, the method comprises a step of measuring the temperature of the skin. When the measured temperature exceeds a temperature safety value, the application of current profile is switched to a safety level, for example less than 1V, such as 0.5V. The temperature safety value may be chosen less than 42° C.

In a preferred embodiments of the iontophoresis method, the method comprises the steps of:
measuring the temperature of the skin, and
measuring the impedance of the composition, and
measuring the pH of the composition.

Then, the device is configured for treating the results and regulating the microcurrent and polarity.

In some embodiments, an iontophoresis composition comprises one or more of vitamin C, vitamin C derivatives, ions of vitamin C, and ions of vitamin C derivatives present in amounts ranging from 0.1% to 30% by weight; one or more silicon materials present in amounts ranging from 0.1% to 30% by weight; and water present in an amount of at least 20% by weight; the iontophoresis composition having an aqueous phase that is at least 30% by weight relative to the total weight of the iontophoresis composition.

In some embodiment, when the measured pH exceeds a pH safety range, for example the range from 4 to 7, the device switches the polarity during a short time to enable to reequilibrate the pH.

In some embodiments of the iontophoresis composition, the composition further comprises one or more ionic polymers present in amounts ranging from 0.01% to 10% by weight; wherein the one or more of vitamin C, vitamin C derivatives, ions of vitamin C, and ions of vitamin C derivatives are present in amounts ranging from 0.1% to 30% by weight.

In some embodiments of the iontophoresis composition, the composition further comprises one or more non-ionic polymers present in amounts ranging from 0.01% to 20% by weight; wherein the one or more of vitamin C, vitamin C derivatives, ions of vitamin C, and ions of vitamin C derivatives are present in amounts ranging from 0.01% to 30% by weight.

In some embodiments of the iontophoresis composition, the composition further comprises a pH ranging from 2 to 7.5.

In some embodiments, the invention also provides a iontophoresis kit comprising:
a iontophoresis composition including,
one or more of vitamin C, vitamin C derivatives, ions of vitamin C, and ions of vitamin C derivatives, for example as described above, and
a iontophoresis device for carrying the iontophoresis method as described above.

The composition may be an aqueous composition.

The iontophoresis kit may be configured such that vitamin C and water are already mixed in the composition when the composition is applied to the skin.

In some embodiments, the iontophoresis device may comprise at least one of a temperature sensor, an impedance sensor, and a pH sensor. The iontophoresis device may comprise at least two of a temperature sensor, an impedance sensor, and a pH sensor. In an embodiment, the iontophoresis device may comprise a temperature sensor, an impedance sensor, and a pH sensor.

The device may be configured such that the application of current profile is reduced to a safety level when a measured value measured by one of the sensors exceeds a safety range or a safety value.

In a preferred embodiment, the method above enable to reduce the spots on the hands and/or on the face and/or on the neck and/or décolleté, for example age spots and/or sunspot and/or freckles and/or spots due to a disease. Then, the above method enables the depigmentation of the skin, especially in zones where the pigmentation is initially too high. After several uses or a single use of the method of the invention, the color of the skin is more uniform and homogeneity is increased.

In another embodiment, the method is used to treat winkles and ageing signs, to improve smoothness, quality of skin and appearance of the skin.

In another embodiment, the method is used to minimize skin anti-aging, and/or pigmentation, and/or volume, and/or sagging wrinkle, and/or event tone and/or spots, and/or to improve firmness, and/or radiance, and/or smoothness, and/or softness of the skin. The method of the invention may be associated with the application of active agents associated to micro current (µcurrent).

Iontophoresis Device Comprising: an Electrode Assembly Including at Least One Electrode and an Aqueous Active Agent In some embodiments, an iontophoresis device comprises an electrode assembly including at least one electrode and an active agent, in particular vitamin C, for example an aqueous active agent composition; and circuitry operably coupled to the electrode assembly and configured to concurrently generate at least a continuous direct current stimulus and a pulsed current stimulus to the same electrode, the continuous direct current stimulus and the pulsed current stimulus of a character and for a duration sufficient to deliver an active agent, in particular vitamin C, for example an active agent composition, to a biological subject.

In some embodiments of the iontophoresis device, the continuous direct current stimulus comprises an average current density ranging from 0.001 mA/cm$^2$ to 0.5 mA/cm$^2$, in particular from 0.01 mA/cm$^2$ to 0.5 mA/cm$^2$.

In some embodiments of the iontophoresis device, the continuous direct current stimulus comprises an average current density of 0.2 mA/cm$^2$.

In some embodiments of the iontophoresis device, the pulsed current stimulus may have an average current density ranging from 0.005 mA/cm$^2$ to 0.5 mA/cm$^2$, in particular from 0.05 mA/cm$^2$ to 0.5 mA/cm$^2$; a pulse duration ranging from 100 microseconds to 500 microseconds, in particular from 200 microseconds to 300 microseconds; and a pulse frequency ranging from 5 Hertz to 500 Hertz, in particular from 100 Hertz to 300 Hertz.

In some embodiments of the iontophoresis device, the pulsed current stimulus comprises an average current density ranging from 0.01 mA/cm$^2$ to 10 mA/cm$^2$; a pulse width ranging from 50 microseconds to 1 milliseconds; and a pulse frequency ranging from 10 Hertz to 500 Hertz; and the duty cycle of pulses ranging from 1% to 90%.

In some embodiments of the iontophoresis device, the pulsed current stimulus comprises an average current density ranging from 0.01 mA/cm$^2$ to 10 mA/cm$^2$; a pulse width ranging from 50 microseconds to 1 milliseconds; and at least one wave packet (or wave train) ranging from 2 to 20 pulses; a frequency of wave packets ranging from 10 Hertz to 500 Hertz; and the duty cycle of pulses ranging from 1% to 90%.

In some embodiments of the iontophoresis device, the pulsed current stimulus comprises an average current density ranging from 0.01 mA/cm$^2$ to 10 mA/cm$^2$; a pulse width ranging from 50 microseconds to 1 milliseconds; and at least one wave packet (or wave train) ranging from 2 to 20 pulses with alternating polarity; a frequency of wave packets ranging from 10 Hertz to 500 Hertz; and the duty cycle of pulses ranging from 1% to 90%.

In some embodiments of the iontophoresis device, the pulsed current stimulus comprises an average current density of 0.2 mA/cm$^2$; an alternating pulse duration of 500 microseconds; and a pulse frequency of 200 Hertz.

In some embodiments of the iontophoresis device, the electrode assembly includes at least one reservoir holding an active agent, in particular an active agent composition, for example an aqueous active agent composition.

In some embodiments of the iontophoresis device, the electrode assembly includes at least one active electrode electrically coupled to a reservoir holding a cosmetic composition, particularly an active composition; for example an active aqueous composition, the electrode assembly operable to transdermally deliver the active agent composition to a biological subject responsive to one or more inputs from the circuitry configured to concurrently generate the continuous direct current stimulus and the pulsed current stimulus.

In some embodiments of the iontophoresis device, the electrode assembly is electrically coupled to at least one power source.

In some embodiments of the iontophoresis device, the electrode assembly includes at least one active electrode assembly and at least one counter electrode assembly.

In some embodiments of the iontophoresis device, the electrode assembly includes at least one reservoir holding a cosmetic composition comprising a face care or body care composition, comprising, in particular, an active agent chosen from humectant or moisturizing active agents, anti-ageing active agents, for example depigmenting active agents, active agents that act on cutaneous microcirculation, or seboregulating active agents, or a composition for making up the face or body, or a hair composition, in particular, a composition for washing the hair, for hair care or conditioning, for temporary form retention or shaping of the hair, for the temporary, semi-permanent or permanent dyeing of the hair, or for relaxing or permanent waving, in particular, a composition for relaxing, dyeing or bleaching the roots and hair, or a composition for the scalp, in particular, an anti-dandruff composition, a composition for preventing hair loss or for promoting regrowth of the hair, an anti-seborrheic composition, an anti-inflammatory composition, an anti-irritation or soothing composition, a mark-preventing composition or a composition for stimulating or protecting the scalp.

The composition may be an aqueous composition.

The iontophoresis device may be configured such that active agent and water are already mixed in the composition when the composition is applied to the skin.

The iontophoresis device may be configured such that active agent and water are mixed only when the iontophoresis device is used.

In some embodiments, the iontophoresis device may comprise at least one of a temperature sensor, an impedance sensor, and a pH sensor. The iontophoresis device may comprise at least two of a temperature sensor, an impedance sensor, and a pH sensor. In an embodiment, the iontophoresis device may comprise a temperature sensor, an impedance sensor, and a pH sensor.

The device may be configured such that the application of current profile is reduced to a safety level when a measured value measured by one of the sensors exceeds a safety range or a safety value.

In a preferred embodiment, the method above enable to reduce the spots on the hands and/or on the face and/or on the neck and/or décolleté, for example age spots and/or sunspot and/or freckles and/or spots due to a disease. Then, the above method enables the depigmentation of the skin, especially in zones where the pigmentation is initially too high. After several uses or a single use of the method of the invention, the color of the skin is more uniform and homogeneity is increased.

In another embodiment, the method is used to treat winkles and ageing signs, to improve smoothness, quality of skin and appearance of the skin.

In another embodiment, the method is used to minimize skin anti-aging, and/or pigmentation, and/or volume, and/or sagging wrinkle, and/or event tone and/or spots, and/or to improve firmness, and/or radiance, and/or smoothness, and/or softness of the skin. The method of the invention may be associated with the application of active agents associated to micro current (µcurrent).

In an embodiment, the active agent is vitamin C.

In some embodiments, an iontophoresis method comprises: concurrently delivering a continuous direct current and a pulsed current to a biological subject, the continuous direct current and the pulsed current of a character and for a duration sufficient to deliver a cosmetic composition to a biological subject.

In some embodiments of the iontophoresis method, concurrently delivering the continuous direct current and the pulsed current to a biological subject includes generating a continuous direct current stimulus having an average current density ranging from 0.01 mA/cm$^2$ to 0.5 mA/cm$^2$.

In some embodiments of the iontophoresis method, concurrently delivering the continuous direct current and the pulsed current to a biological subject includes generating a continuous direct current stimulus having an average current density of 0.2 mA/cm$^2$.

In some embodiments of the iontophoresis method, concurrently delivering the continuous direct current and the pulsed current to a biological subject includes generating a pulsed current stimulus having an average current density ranging from 0.01 mA/cm$^2$ to 10 mA/cm$^2$; a pulse duration ranging from 50 microseconds to 1 milliseconds; and a pulse frequency ranging from 10 Hertz to 500 Hertz; and the duty cycle of pulses ranging from 1% to 90%.

In some embodiments of the iontophoresis method, concurrently delivering the continuous direct current and the pulsed current to a biological subject includes generating a pulsed alternating current stimulus having an average current density of 0.2 mA/cm$^2$; a pulse duration of 500 microseconds; and a pulse frequency of 200 Hertz.

In some embodiments of the iontophoresis method, the pulsed current comprises an average current density ranging from 0.01 mA/cm$^2$ to 10 mA/cm$^2$; a pulse width ranging from 50 microseconds to 1 milliseconds; and at least one wave packet (or wave train) ranging from 2 to 20 pulses; a frequency of wave packets ranging from 10 Hertz to 500 Hertz; and the duty cycle of pulses ranging from 1% to 90%.

In some embodiments of the iontophoresis method, the pulsed current comprises an average current density ranging from 0.01 mA/cm$^2$ to 10 mA/cm$^2$; a pulse width ranging from 50 microseconds to 1 milliseconds; and at least one wave packet (or wave train) ranging from 2 to 20 pulses with alternating polarity; a frequency of wave packets ranging from 10 Hertz to 500 Hertz; and the duty cycle of pulses ranging from 1% to 90%.

In some embodiments of the iontophoresis method, concurrently delivering the continuous direct current and the pulsed current to a biological subject includes generating a pulsed current having sinusoidal waveforms, non-sinusoidal waveforms, or combinations thereof.

In some embodiments of the iontophoresis method, concurrently delivering the continuous direct current and the pulsed current to a biological subject includes generating a pulsed current having periodic square waveforms, rectangular waveforms, saw tooth waveforms, spiked waveforms, trapezoidal waveforms, triangle waveforms, or combinations thereof.

In some embodiments of the iontophoresis method, the method further comprises delivering a cosmetic composition chosen from: a face care or body care composition, comprising, in particular, an active agent chosen from humectant or moisturizing active agents, anti-ageing active agents, for example depigmenting active agents, active agents that act on cutaneous microcirculation, or seboregulating active agents, or a composition for making up the face or body.

In some embodiments of the iontophoresis method, the method further comprises:

transdermally delivering an active agent present in amounts ranging from 0.01% to 100% by weight, preferably from 0.5% to 60% by weight.

In some embodiments of the iontophoresis method, the method comprises a step of measuring at least one of the temperature of the skin, the impedance of the skin, and a pH of the composition.

In some embodiments of the iontophoresis method, the application of current profile is reduced to a safety level when a measured value measured by one of the sensors exceeds a safety range or a safety value.

In some embodiments of the iontophoresis method, the method comprises a step of measuring the pH of the composition. When the measured pH exceeds a pH safety range, the application of current profile is switched to a safety level, for example a safety level less than 1V, such as 0.5V. The pH safety range may be pH 4 to 7. In some embodiment, when the measured pH exceeds a pH safety range, for example the range from 4 to 7, the device switches the polarity during a short time to enable to reequilibrate the pH.

In some embodiments of the iontophoresis method, the method comprises a step of measuring the impedance of the skin. When the measured impedance exceeds an impedance safety range, the application of current profile is reduced to a safety level to avoid adverse event. The safety level may be less than 1V, such as 0.5V. The impedance safety range may be 50Ω to 1 MΩ.

In some embodiments of the iontophoresis method, the method comprises a step of measuring the temperature of the skin. When the measured temperature exceeds a temperature safety value, the application of current profile is switched to a safety level, for example less than 1V, such as 0.5V. The temperature safety value may be chosen less than 42° C.

In a preferred embodiment of the iontophoresis method, the method comprises the steps of:

measuring the temperature of the skin, and
measuring the impedance of the composition, and
measuring the pH of the composition.

Then, the device is configured for treating the results and regulating the microcurrent and polarity.

DESCRIPTION OF THE DRAWINGS

The foregoing aspects and many of the attendant advantages of the disclosed subject matter will become more readily appreciated as the same become better understood by reference to the following detailed description, when taken in conjunction with the accompanying drawings, wherein.

DETAILED DESCRIPTION

Figure 1:
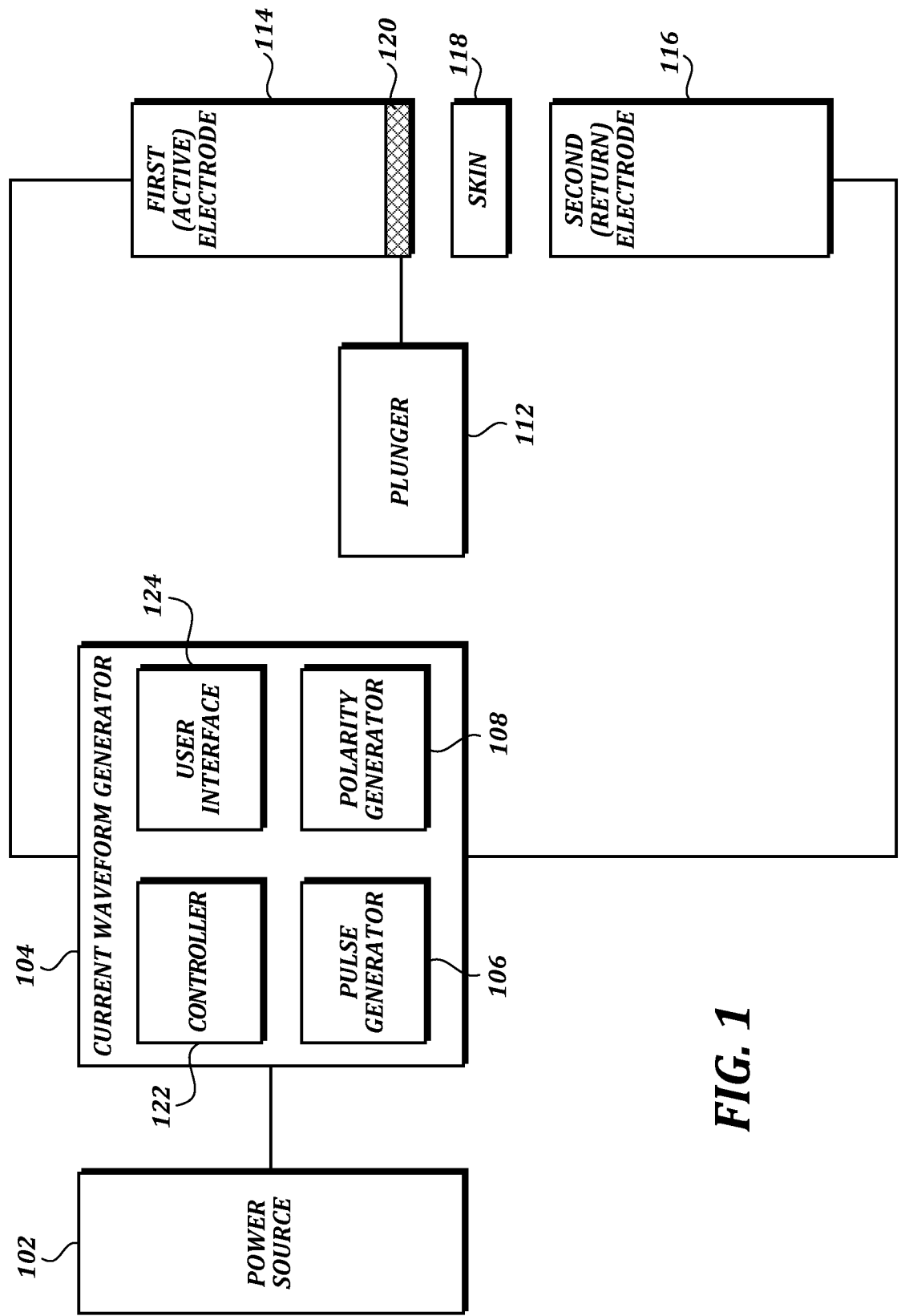
FIG. 1 is a schematic illustration of an iontophoresis device.

Vitamin C and its various forms (e.g., ascorbic acid, ascorbic acid salts, L-ascorbic acid, ascorbate, 2-oxo-L-threo-hexono-1,4-lactone-2,3-enediol, R)-3,4-dihydroxy-5-((S)-1,2-dihydroxyethyl)furan-2(5H)-one, oxidized forms ascorbic acid, anions of ascorbic acid dehydroascorbic, and the like) may have one or more beneficial uses. For example, vitamin C may act as an antioxidant against oxidative stress in humans. Vitamin C may also act as both a reducing agent and a free radical scavenger. One problem, however, is that vitamin C has a very low solubility in non-aqueous media. Additionally, if dissolved, vitamin C is easily oxidized and therefore loses function. Accordingly, some embodiments are directed to technologies and methodologies for transdermally delivering an active agent composition, for example an aqueous active agent composition, such as vitamin C, to a biological subject.

Iontophoresis is the process of conducting an electrical current for the purpose of transporting charged molecules into the skin. The technique involves the application of a mild electrical current to a charged molecule by using a similarly charged electrode as the molecule of interest to produce a repulsive effect that drives the charged molecules away from the electrode and into the skin. In some embodiments, the effect of simple ionization (electromigration) is the main mechanism by which iontophoresis produces its transport properties. However, there are additional mechanisms called electroosmosis and electroporation that are produced by an electrical current. Electroosmosis induces a flow of solvent that carries uncharged molecules in the anode-to-cathode direction. In some embodiments, "iontophoresis" is the technique of using an electrical current to deliver molecules into the skin regardless of whether transport of the molecule is via electromigration or electroosmosis or electroporation.

Since many active molecules in skin care compositions have ionic forms, iontophoresis can be an effective tool for the administration of these active molecules. Vitamin C is also referred to as L-ascorbic acid, or by the systematic (International Union of Pure and Applied Chemistry) names, 2-oxo-L-threo-hexono-1,4-lactone-2,3-enediol or (R)-3,4-dihydroxy-5-((S')-1,2-dihydroxyethyl)furan-2(5H)-one.

Vitamin C is a negatively charged molecule at the physiological pH, thus, the inventor recognizes that vitamin C would be a good candidate for administration via iontophoresis. Accordingly, methods using electrical waveform stimuli for the administration of vitamin C into the skin are disclosed. In some embodiments, the administration of vitamin C is conducted on live, human beings. In some embodiments, the administration of vitamin C is conducted on any biological subject. In some embodiments, biological subjects include, but are not limited to, mammals, including human beings.

The efficacy of topical application of vitamin C is low as it has very low solubility in a non-aqueous medium, and if dissolved, vitamin C is easily oxidized and therefore loses function. In some embodiments, in cosmetics, vitamin C is used in compositions containing polymers to render the molecule stable. Although the presence of such substances usually plays a positive role in the formulation properties, they may also limit the efficient delivery of vitamin C into the skin. Accordingly, also disclosed are compositions formulated to increase the penetration of vitamin C, preferably in the ascorbic acid form, into skin by electrical currents, preferably by iontophoresis. Analysis of skin penetration profiles suggests that galvanic current (also referred to as direct current (DC)) coupled with pulsed current significantly improved the topical transport of active agents. In some embodiments, such active agents include vitamin C in the ascorbic acid form that mainly includes the facilitated absorption phase in which the penetration of the molecule is efficiently enhanced by "iontophoresis." The skin penetration rate increases with respect to the type of formulation applied principally due to the impact of the formulation components, in addition to the physicochemical properties of vitamin C.

Referring to FIG. 1, an iontophoresis device and electrode assembly is schematically illustrated. In some embodiments, the iontophoresis device and electrode assembly includes a power source 102, a current waveform generator 104, a first (active) electrode 114, a second (counter or return) electrode 116, a plunger 112, and a reservoir 120 at the end of the first electrode 114. It is to be appreciated that iontophoresis devices are available with additional features or fewer features. Therefore, other devices may include many other components that are not being shown or exclude some of the components that are shown. The purpose of FIG. 1 is to illustrate and describe some of the major functional components of an iontophoresis device used to carry out one or more of the various embodiments of the methods for the application of vitamin C compositions or other active agent compositions disclosed herein. It is to be appreciated that implicit and inherent in FIG. 1 is the circuitry used to carry out the functions of the iontophoresis device. In some embodiments, the iontophoresis device is packaged as a hand-held device that is suitable for carrying in one hand during treatment. Treatment using hand-held devices includes constantly moving the iontophoresis device over the skin so that the active electrode 114 is moved across the surface of the skin while making contact. In some embodiments, the iontophoresis device is packaged as a stationary desk-top device, and the active electrode 114 is stationary and applied to a single location on the skin, such as through an adhesive. The major functional components of the iontophoresis device will now be described.

In some embodiments, the iontophoresis device includes a power source 102. A suitable power source would be any power source that can generate electrical current to power the various other circuits and devices. In some embodiments, a battery is used as the power source. Additionally, in some embodiments, an alternating power source coupled to a transformer can be connected to the power source 102. In some embodiments, the iontophoresis device is plugged into a wall socket. In some embodiments, the power source 102 produces continuous direct current. In some embodiments, circuitry is used to generate electrical waveforms other than continuous direct current. The power source 102 has a negative pole and a positive pole. Generally, negative polarity will be applied to the first electrode 114. However, through circuitry and electrical devices, such as switches, the polarities of the first 114 and second 116 electrodes can be reversed momentarily to achieve pulse and alternating current waveforms.

In some embodiments, the power source 102 is connected to the current waveform generator 104. The current waveform generator 104 functions to generate various types of current waveforms. In some embodiments, the current waveform generator 104 generates the waveforms through hardware and software, such as circuitry, described herein. In some embodiments, the waveform generator 104 includes circuitry operably coupled to an electrode assembly, and the circuitry is configured to concurrently generate at least a continuous direct current stimulus and a pulsed current stimulus to the same electrode, the continuous direct current stimulus and the pulsed current stimulus of a character and for a duration sufficient to deliver a cosmetic composition to a biological subject. The current generator 104 is connected to the first 114 and the second 116 electrodes and is able to apply a potential across the electrodes to supply electrical current stimuli in various waveforms described herein. Toward that end, the current waveform generator 104 includes a pulse generator 106 and a polarity generator 108. In some embodiments, functionally, the pulse generator 106 generates pulses of current of controlled amplitude and duration. In some embodiments, functionally, the polarity generator 108 controls the polarity at the first electrode 114 and second electrode 116. In some embodiments, the polarity generator 108 maintains the polarities of the first 114 and second 116 electrodes constant. In some embodiments, the polarity generator 108 applies zero polarity to the first and second 116 electrodes. In some embodiments, the polarity generator 108 applies the polarity to the first and second 116 electrodes in pulses at a predefined rate and duration. In some embodiments, the polarity generator 108 reverses the polarities of the first 114 and second 116 electrodes at a predefined rate or interval. In some embodiments, the polarity generator 116 is configured to apply constant polarity, pulses, or reverse polarity for predefined durations, sequentially or in any order.

In some embodiments, the iontophoresis device will include a controller 122. In some embodiments, functionally, the controller 122 will receive input from the user interface 124 and, in conjunction with the pulse generator 106 and the polarity generator 108, control the current density waveforms at the specifications input by the user/operator. In some embodiments, the controller 122, pulse generator 106, and polarity generator 108 are implemented in hardware components, such as analog circuitry, digital circuitry, microprocessors, or combinations thereof, or software components.

In some embodiments, the controller 122 has instructions for guiding a user to input the various parameters depending on the waveform stimulus that is to be applied. The user interface 124 can prompt the user for the information. In some embodiments, the controller 122 will request the user to select the stimulus output from a constant (DC) value, a pulse wave, or both a constant value and a pulse wave for the current density stimulus output waveform. Once the controller 122 receives input of the one or more stimulus wave types, the controller 122 prompts the user on the user interface 124 for parameters corresponding to the selected wave output type or types.

In some embodiments, the iontophoresis device includes the user interface 124. In some embodiments, functionally, the user interface 124 is for entry of data relating to the waveform types to be applied as electrical stimuli. In some embodiments, the user interface 124 includes an alphanumeric keyboard and display. In some embodiments, the user interface 124 includes directional arrow buttons and an enter button to enter data into memory. In some embodiments, the alphanumeric keyboard is implemented as a touch screen display. In some embodiments, the input of wave parameters is through the use of text boxes. In some embodiments, the input of wave parameters is through the use of scrolling menus.

Regardless of the manner of data entry, in some embodiments, the user interface 124 communicates a variety of prompts for the user to input information. In some embodiments, the user interface 124 prompts the user to input the duration of the treatment step. In some embodiments, the duration of the treatment step is the sum of time of the application of an electrical current of any one or more wave types and includes the time when electrical current is off for pulse waves. For example, a pulse wave set with a duty cycle of 50% has the electrical current off during 50% of the time, meaning that each pulse is one-half of each pulse cycle. However, the treatment duration will include the off period of the pulse cycle.

In some embodiments, the user interface 124 provides options to allow the user to input whether the current density output will be continuous direct current, pulse current, alternating pulse current, or any combination, and the duration of each wave type. In some embodiments, the user interface 124 prompts the user whether different wave types are superimposed on each other. For example, a pulse wave can be superimposed on a continuous direct current wave. In some embodiments, the user interface 124 prompts the user whether different wave types are combined in sequence. In some embodiments, the user interface 124 prompts the user to input the current density values to output for each wave type. In some embodiments, the current density is input as average current density, root mean square current density, or peak current density. In some embodiments, the user interface 124 prompts the user to input the polarity at the first electrode 114, including positive, negative, or both for alternating, with the corresponding constant or pulsed current output. In some embodiments, the user interface 124 prompts the user to input the electrodes' cross-sectional areas. In some embodiments, the user interface 124 prompts the user to input skin temperature. In some embodiments, the user interface 124 prompts the user to input the frequency of pulses, the maximum and minimum amplitudes of pulses, and the duration of pulses. In some embodiments, the user interface 124 prompts the user to input the % duty cycle of unidirectional pulses. In some embodiments, the user interface 124 prompts the user to input the % duty cycle of respective bipolar pulses. In some embodiments, the user interface 124 prompts the user to specify the time between pulses. In some embodiments, the user interface 124 prompts the user to specify the duration of a wave packet (wave train), and the frequency of the wave packets. In some embodiments, the user interface 124 prompts the user to specify the number of pulses in a wave packet (wave train). In some embodiments, the user interface 124 prompts the user to input the pulse wave shape, including periodic square waveforms, rectangular waveforms, saw tooth waveforms, spiked waveforms, trapezoidal waveforms, or triangle waveforms. In some embodiments, the user interface 124 prompts the user to input the treatment area. In some embodiments, the user interface 124 prompts the user to specify whether to apply alternating negative and positive pulses. In some embodiments, the user interface 124 prompts the user to specify whether pulses are to be unipolar or bipolar.

A unipolar pulse means that pulsed electrical current travels in one direction. A bipolar pulse means that pulsed electrical current travels in two directions or reverses directions. In some embodiments, the user interface 124 prompts the user to specify a ratio of negative to positive pulses or a ratio of positive to negative pulses. In some embodiments, the user interface 124 prompts the user whether to combine any continuous direct current waveform with any pulse waveform to provide two or more different waveforms concurrently. In some embodiments, the user interface 124 prompts the user to apply two or more waveforms concurrently, synchronously, sequentially, or alternately. In some embodiments, the user interface 124 prompts the user to input the duration of each waveform and the cycle time of each waveform if the waveforms alternate. In some embodiments, the user interface 124 prompts the user for a pulse interval duration.

In some embodiments, when using two or more waveforms in a single treatment, the user interface 124 prompts the user to specify the treatment durations of the different waveforms, and how often each waveform cycles. In some embodiments when continuous direct current is used concurrently with a pulse wave, the user interface 124 prompts the user to specify the parameters of the pulse wave.

In some embodiments, the controller 122 carries out logic routines to direct the user interface 124 to present to the user the appropriate prompts so that the wave type information is entered. The controller 122 then uses the wave type parameters to generate, via the circuitry, including but not limited to the pulse generator 106 and the polarity generator 108, the appropriate stimulus wave according to the user entered parameters.

In some embodiments, the first electrode 114, also referred to as the active electrode, is connected to the power source 102 through the waveform generator 104. The first electrode 114 includes a reservoir 102 on the end thereof to hold a vitamin C composition or any active agent composition. In some embodiments, the reservoir 120 is a hollow indentation on the end of the first electrode 114, wherein the reservoir is used to contain a gel or gel-like vitamin C composition. Alternatively, in some embodiments, the reservoir 120 is an absorbent material to contain the vitamin C composition. In some embodiments, generally, the design of the first electrode 114 contemplates the first electrode 114 having negative polarity. When the iontophoresis device is packaged as a hand-held device, the first electrode 114 is provided with a type of roll-on applicator, such as a ball and socket fed by the plunger 112.

The skin 118 represents the load on the system.

In some embodiments, the second electrode 116, also referred to as the counter or return electrode, is connected to the power source 102 through the waveform generator 104. The polarity of the second electrode 116 is maintained by the waveform generator 104 to be the opposite of the polarity of the first electrode 114. In some embodiments, generally, the design of the second electrode 116 contemplates the second electrode 116 having positive polarity. In some embodiments, the second electrode 116 is a hand-held electrode that is held by the person receiving the treatment. In other embodiments, the second electrode 116 has an insulated cover and an exposed tip so that the second electrode is held by the device user and applied by the user on the skin of the person receiving the treatment.

In some embodiments, the reservoir 120 on the first electrode 114 is connected to a plunger 112. In some embodiments, functionally, the plunger 112 replenishes the vitamin C composition or any active agent composition in the reservoir 120. In some embodiments, the plunger 112 includes a piston and push pod within a cylindrical container. In some embodiments, the plunger 112 can be operated by a trigger mechanism that is operated during treatment by the user of the iontophoresis device.

In some embodiments, an iontophoresis device includes active (donor) and return (counter) electrode assemblies, a skin contacting layer, and an active agent layer. In some embodiments, an iontophoresis device includes active and return electrode assemblies having a multi-laminate construction. In some embodiments, an iontophoresis device includes electrode assemblies with a multi-laminate construction configured to deliver an active agent composition through passive diffusion or iontophoresis.

In some embodiments, an iontophoresis device includes active and return electrode assemblies, each formed by multiple layers of polymeric matrices. In some embodiments, an iontophoresis device includes electrode assemblies having a conductive resin film electrode layer, a hydrophilic gel reservoir layer, an aluminum or silver foil conductor layer, and an insulating backing layer.

In some embodiments, an iontophoresis device comprises an iontophoresis patch design. In some embodiments, an iontophoresis device comprises an iontophoresis multi-laminate design. In some embodiments, an iontophoresis device comprises an iontophoresis face mask design. In some embodiments, an iontophoresis device comprises an iontophoresis flexible substrate design.

In some embodiments, an electrode assembly includes at least one electrode and one or more compositions with an agent stored in a reservoir such as a cavity, a gel, a laminate, a membrane, a porous structure, a matrix, a substrate, or the like. Non-limiting examples of active agents include electrically neutral agents, molecules, or compounds capable of being delivered via electro-osmotic flow. In some embodiments, neutral agents are carried by the flow of, for example, a solvent during electrophoresis. In some embodiments, an iontophoresis device includes an electrode and a reservoir containing an effective amount of a vitamin C composition or any agent composition.

In some embodiments, a reservoir includes any form or matter employed to retain an element, a composition, a compound, active agent, a pharmaceutical composition, and the like, in a liquid state, solid state, gaseous state, mixed state or transitional state. In some embodiments, a reservoir includes one or more ion exchange membranes, semi-permeable membranes, porous membranes or gels capable of at least temporarily retaining an element, a composition, a compound, active agent, a pharmaceutical composition, electrolyte solution, and the like.

In some embodiments, a reservoir includes one or more cavities formed by a structure. In some embodiments, a reservoir serves to retain an element, a composition, a compound, active agent, a pharmaceutical composition, electrolyte solution, and the like prior to the discharge of such by electromotive force or current into a biological interface. In some embodiments, an electrode assembly includes one or more ion exchange membranes that may be positioned to serve as a polarity selective barrier between the active agent reservoir and a biological interface.

In some embodiments, an electrode assembly includes an electrode and a reservoir containing an effective amount of a vitamin C composition or any active agent composition, for example an aqueous active agent composition.

In some embodiments, the iontophoresis device includes circuitry that is coupled to the active electrode assembly, wherein the circuitry is configured to generate at least current stimuli from pulsed or continuous in a concurrent manner. In some embodiments, the circuitry is included in the iontophoresis device and the current waveform generator 104 illustrated in FIG. 1. In some embodiments, circuitry applies a potential across the active and counter electrodes, the circuitry generates a current stimulus of selected wave form, amplitude, duration, polarity. In some embodiments, the circuitry causes an electrical repulsion of active agents in order to deliver the active agent to the biological subject.

In some embodiments, circuitry includes, among other things, one or more computing devices such as a processor (e.g., a microprocessor, a quantum processor, qubit processor, etc.), a central processing unit (CPU), a digital signal processor (DSP), an application-specific integrated circuit (ASIC), a field programmable gate array (FPGA), or the like, or any combinations thereof, and can include discrete digital or analog circuit elements or electronics, or combinations thereof. In some embodiments, a module includes one or more ASICs having a plurality of predefined logic components. In some embodiments, a module includes one or more FPGAs, each having a plurality of programmable logic components.

In some embodiments, circuitry includes one or more electric circuits, printed circuits, electrical conductors, electrodes, electrocautery electrodes, cavity resonators, conducting traces, ceramic patterned electrodes, electro-mechanical components, transducers, and the like.

In some embodiments, circuitry includes one or more components operably coupled (e.g., communicatively, electromagnetically, magnetically, ultrasonically, optically, inductively, electrically, capacitively coupled, wirelessly coupled, or the like) to each other. In some embodiments, circuitry includes one or more remotely located components. In some embodiments, remotely located components are operably coupled, for example, via wireless communication. In some embodiments, remotely located components are operably coupled, for example, via one or more communication modules, receivers, transmitters, transceivers, or the like.

In some embodiments, circuitry includes memory that, for example, stores instructions or information. Non-limiting examples of memory include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of memory include Erasable Programmable Read-Only Memory (EPROM), flash memory, or the like. In some embodiments, memory is coupled to, for example, one or more computing devices by one or more instructions, information, or power buses.

In some embodiments, circuitry includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In some embodiments, a module includes one or more user input/output components that are operably coupled to at least one computing device configured to control (electrical, electromechanical, software-implemented, firmware-implemented, or other control, or combinations thereof) at least one parameter associated with, for example, determining one or more tissue thermal properties responsive to detected shifts in turn-ON voltage.

In some embodiments, circuitry includes a computer-readable media drive or memory slot that is configured to accept signal-bearing medium (e.g., computer-readable memory media, computer-readable recording media, or the like). In some embodiments, a program for causing a system to execute any of the disclosed methods can be stored on, for example, a computer-readable recording medium, a signal-bearing medium, or the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, or the like, as well as transmission type medium such as a digital or an analog communication medium (e.g., a fiber optic cable, a waveguide, a wired communications link, a wireless communication link (e.g., receiver, transmitter, transceiver, transmission logic, reception logic, etc.). Further, non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

In some embodiments, circuitry includes acoustic transducers, electroacoustic transducers, electrochemical transducers, electromagnetic transducers, electromechanical transducers, electrostatic transducers, photoelectric transducers, radioacoustic transducers, thermoelectric transducers, ultrasonic transducers, and the like.

In some embodiments, circuitry includes electrical circuitry operably coupled with a transducer (e.g., an actuator, a motor, a piezoelectric crystal, a Micro Electro Mechanical System (MEMS), etc.). In some embodiments, circuitry includes electrical circuitry having at least one discrete electrical circuit, electrical circuitry having at least one integrated circuit, or electrical circuitry having at least one application specific integrated circuit. In some embodiments, circuitry includes electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs.

In some embodiments, circuitry includes one or more sensors configured to detect at least one physiological characteristic associated with a biological subject.

Having described the iontophoresis device and the circuitry, in some embodiments, an iontophoresis device comprises an electrode assembly including at least one electrode and a cosmetic composition; and circuitry is operably coupled to the electrode assembly and configured to concurrently generate at least a continuous direct current stimulus and a pulsed current stimulus to the same electrode, the continuous direct current stimulus and the pulsed current stimulus of a character and for a duration sufficient to deliver a cosmetic composition to a biological subject.

In some embodiments, during operation, the iontophoresis device includes circuitry configured to generate a continuous direct current stimulus having an average current density ranging from 0.01 mA/cm$^2$ to 0.5 mA/cm$^2$.

In some embodiments, the iontophoresis device includes circuitry configured to generate a continuous direct current stimulus having an average current density of 0.2 mA/cm$^2$.

In some embodiments, the iontophoresis device includes circuitry configured to generate a pulsed current stimulus having an average current density ranging from 0.01 mA/cm$^2$ to 10 mA/cm$^2$, a pulse width ranging from 50 microseconds to 1 milliseconds, and a pulse frequency ranging from 10 Hertz to 500 Hertz, and the duty cycle of pulses ranging from 1% to 90%.

In some embodiments, the iontophoresis device includes circuitry configured to generate a pulsed current stimulus having an average current density ranging from 0.01 mA/cm$^2$ to 10 mA/cm$^2$, a pulse width ranging from 50 microseconds to 1 milliseconds, at least one wave packet (or wave train) having from 2 to 20 pulses; a frequency of the wave packet ranging from 10 Hertz to 500 Hertz, and a duty cycle of pulses ranging from 1% to 90%.

In some embodiments, the iontophoresis device includes circuitry configured to generate a pulsed current stimulus having an average current density ranging from 0.01 mA/cm$^2$ to 10 mA/cm$^2$, a pulse width ranging from 50 microseconds to 1 milliseconds, at least one wave packet (or wave train) ranging from 2 to 20 pulses with alternating polarity, a frequency of the wave packet ranging from 10 Hertz to 500 Hertz, and a duty cycle of pulses ranging from 1% to 90%.

In some embodiments, the iontophoresis device includes circuitry configured to generate a pulsed current stimulus having an average current density of 0.2 mA/cm$^2$, an alternating pulse duration of 500 microseconds, and a pulse frequency of 200 Hertz.

In some embodiments of the iontophoresis device, the electrode assembly includes at least one reservoir holding an active agent composition, for example an aqueous active agent composition.

In some embodiments of the iontophoresis device, the electrode assembly includes at least one active electrode electrically coupled to a reservoir holding a cosmetic composition, particularly an active agent composition, for example an active agent aqueous composition; the electrode assembly operable to transdermally deliver the active agent composition to a biological subject responsive to one or more inputs from the circuitry configured to concurrently generate the continuous direct current stimulus and the pulsed current stimulus.

In some embodiments of the iontophoresis device, the electrode assembly is electrically coupled to at least one power source.

In some embodiments of the iontophoresis device, the electrode assembly includes at least one active electrode assembly and at least one counter electrode assembly.

In some embodiments of the iontophoresis device, the electrode assembly includes at least one reservoir holding a cosmetic composition comprising a face care or body care composition, comprising, in particular, an active agent chosen from humectant or moisturizing active agents, anti-ageing active agents, for example depigmenting active agents, active agents that act on cutaneous microcirculation, or seboregulating active agents, or a composition for making up the face or body, or a hair composition, in particular, a composition for washing the hair, for hair care or conditioning, for temporary form retention or shaping of the hair, for the temporary, semi-permanent or permanent dyeing of the hair, or for relaxing or permanent waving, in particular, a composition for relaxing, dyeing or bleaching the roots and hair, or a composition for the scalp, in particular, an anti-dandruff composition, a composition for preventing hair loss or for promoting regrowth of the hair, an anti-seborrheic composition, an anti-inflammatory composition, an anti-irritation or soothing composition, a mark-preventing composition or a composition for stimulating or protecting the scalp.

Figure 2:
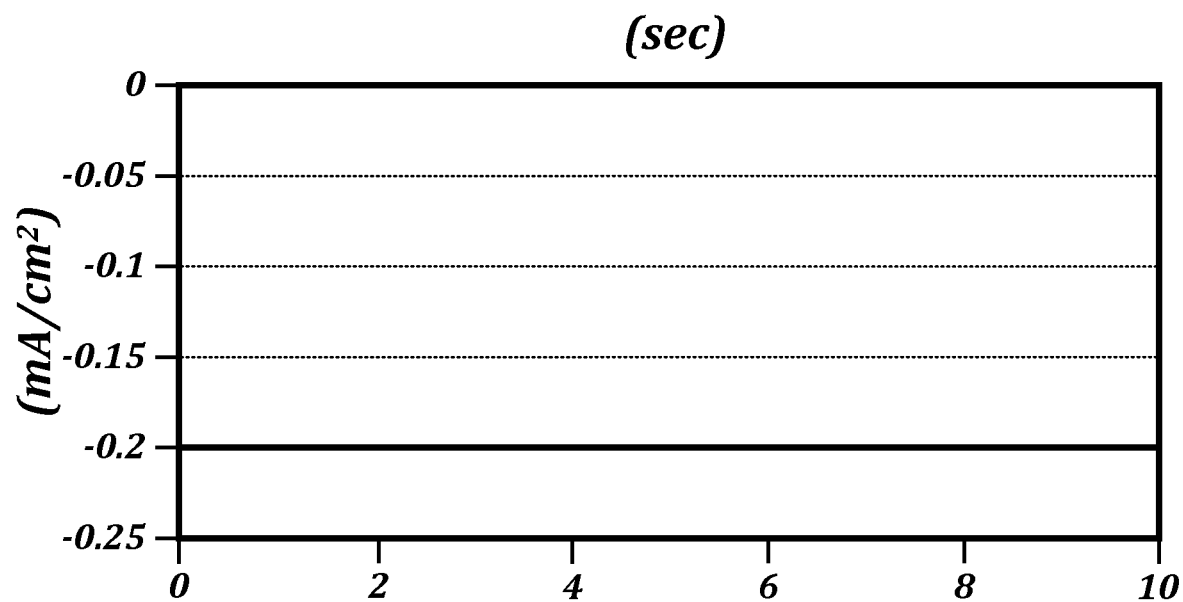
FIG. 2 is a plot of an electrical waveform stimulus in accordance with one embodiment.
Figure 3:
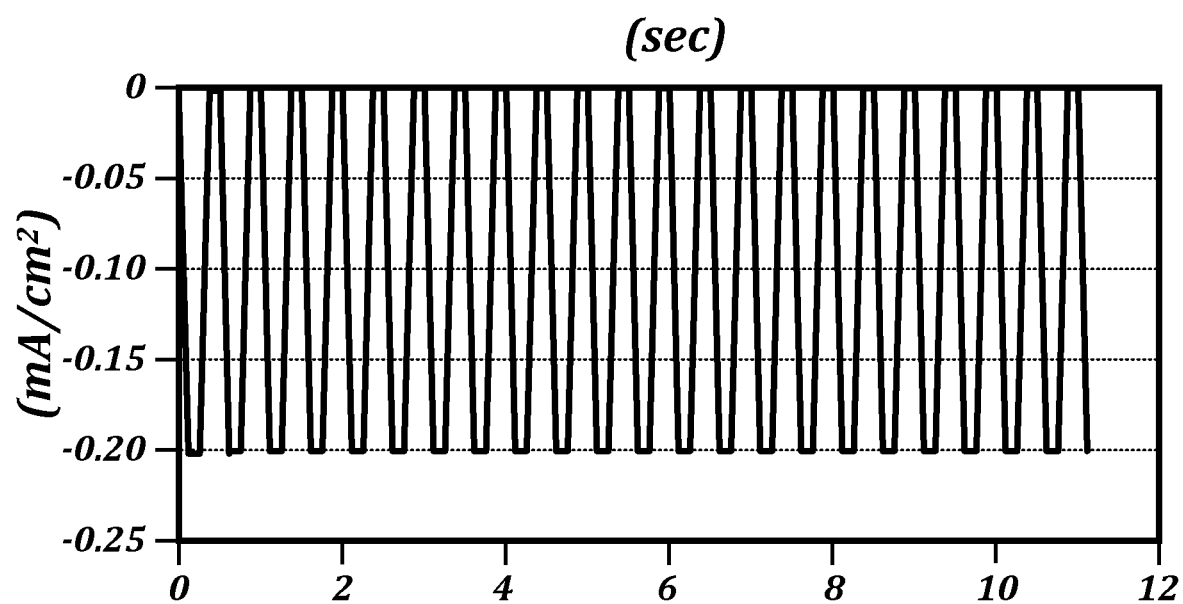
FIG. 3 is a plot of an electrical waveform stimulus in accordance with one embodiment.
Figure 4:
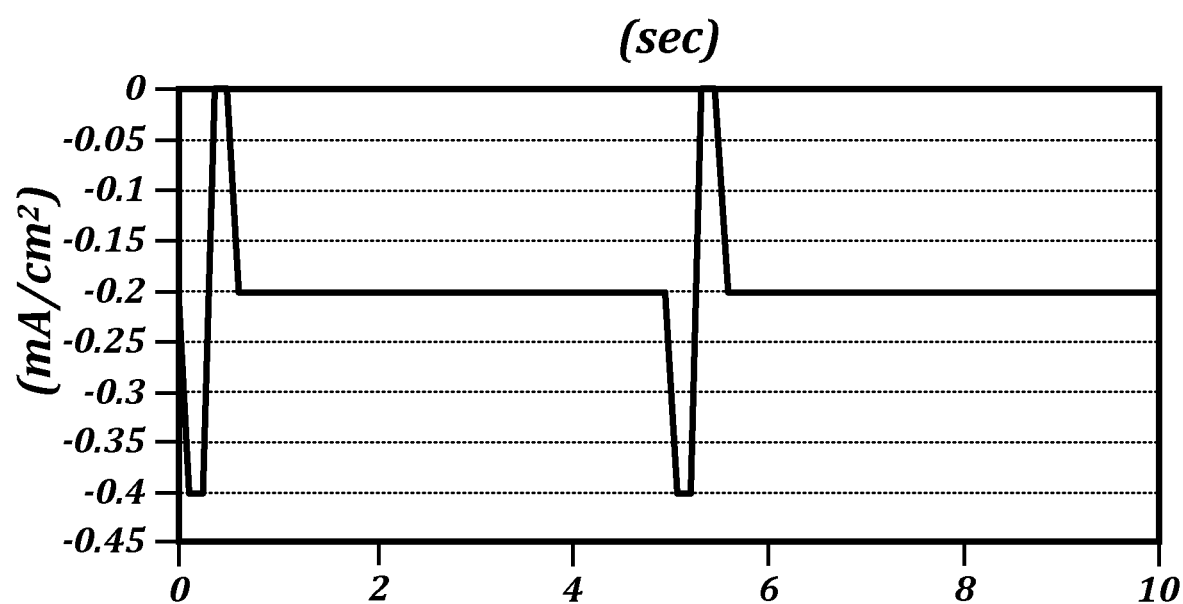
FIG. 4 is a plot of an electrical waveform stimulus in accordance with one embodiment.

FIGS. 2-4 illustrate embodiments of electrical stimuli of representative current density waveforms generated by the circuitry of the iontophoresis device to administer vitamin C or any other aqueous active agent composition.

Referring to FIG. 2, a first current density waveform is illustrated for iontophoresis. FIG. 2 illustrates one embodiment of a waveform that can be generated by the circuitry and iontophoresis device of FIG. 1. FIG. 1 shows a continuous direct current waveform stimulus. The current density waveform is controlled an average constant value for the duration or any part of the iontophoresis treatment. In some embodiments, a current density waveform controlled at a constant value is referred to as continuous direct current, and the terms "direct current," "DC current," "galvanic current," and "DC" are interchangeable. In some embodiments, a negative current density means that the polarity at the first electrode 114 is negative. The second electrode 116 has positive polarity when the first electrode has negative polarity. Following convention, this means that current flows from the second positive electrode 116 to first negative electrode 114. Conversely, when the first electrode 114 has positive polarity and the second electrode 116 has negative polarity, current flows from the first positive electrode 114 to the second negative electrode 116, and this will be represented on a graph by a positive value of current density. Conventionally, electrons will be defined to flow in the opposite direction to current, i.e., from negative polarity to positive polarity. Current density is defined as ampere units per area units (of the cross section of the active electrode).

While FIG. 2 depicts a certain continuous direct current density value and duration, it should be appreciated that the illustrated values are exemplary. In some embodiments of the continuous direct current waveform of FIG. 2, the average current density is controlled at or below 0.5 mA/cm$^2$. In some embodiments of the continuous direct current waveform of FIG. 2, the average current density is controlled at or below 0.2 mA/cm$^2$. In some embodiments of the continuous direct current waveform of FIG. 2, the average current density is controlled between 0.01 mA/cm$^2$ to 0.5 mA/cm$^2$. In some embodiments of the continuous direct current waveform of FIG. 2, the average current density is controlled at any one of the following values, 0.01, 0.05, 0.1, 0.15, 0.2, 0.25, 0.3, 0.35, 0.4, 0.45, 0.5 mA/cm$^2$ or in a range between any two values serving as endpoints. In some embodiments of the continuous direct current waveform of FIG. 2, the amplitude is controlled at any of the above values and electrical current is applied for a duration of at least 1 minute. In some embodiments of the continuous direct current waveform of FIG. 2, the amplitude is controlled at any of the above values and electrical current is applied for a duration of from 10 to 20 minutes. In some embodiments of the continuous direct current waveform of FIG. 2, the amplitude is controlled at any of the above values and electrical current is applied for a duration (in minutes) of 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, 60, or any range between any two values serving as endpoints. In some of the embodiments of the continuous direct current waveform of FIG. 2, the first electrode 114 is negative and the second electrode 116 is positive for duration of the waveform.

Referring to FIG. 3, a second current density waveform is illustrated for iontophoresis. FIG. 3 illustrates one embodiment of a waveform that can be generated by the circuitry and the iontophoresis device of FIG. 1. FIG. 3 shows a pulse wave. The current density waveform is controlled in negative pulses (polarity is negative at electrode 114) for the duration or any part of the iontophoresis treatment. In some embodiments, the polarity can be reversed. The pulses of FIG. 3 are unipolar, meaning that current travels in one direction. A pulse of FIG. 3 has a maximum amplitude. The pulse waveform will increase from a minimum amplitude, reach the maximum amplitude, and then decrease to the minimum amplitude, reside at the minimum amplitude, and the cycle will repeat. In some embodiments, a pulse is counted starting from the minimum amplitude, reaching the maximum amplitude, and then returning to the minimum amplitude. Thus, a pulse does not include the period of the minimum amplitude. In some embodiments, a pulse cycle does include the period at the minimum amplitude. In some embodiments, the durations of the maximum and minimum amplitudes are the same.

In some embodiments, the pulse wave is expressed to have a % duty cycle. In some embodiments, expressing a % duty cycle with respect to a pulse wave means that the electrical current is on for the % duty cycle. For example, 50% duty cycle means electrical current is on for 50% and off for 50% of the pulse cycle, 30% duty cycle means electrical current is on for 30% and off for 70% of the pulse cycle. In some embodiments, the % duty cycle of unidirectional pulses is 5, 10, 15, 20, 25, 30, 35, 40, 45, 50, 55, 60, 65, 70, 75, 80, 85, 90, 95, or any range between any two values serving as endpoints. In some embodiments, the % duty cycle of a respective bipolar pulse is 0.01, 5, 10, 15, 20, 25, 30, 35, 40, 45, 50, 55, 60, 65, 70, 75, 80, 85, 90, 95, 100 or any range between any two values serving as endpoints. In some embodiments, the duty cycle of pulses ranges from 1% to 90%. In some embodiments, the pulse, meaning the "on" period can be expressed as a duration having units of time. In some embodiments, the pulse "off" period can be expressed as a duration. In some embodiments, the pulse wave will be expressed in hertz, meaning cycles per second. In some embodiments, the pulses can be reversed by alternating the polarities of the first and second electrodes between negative and positive. In some embodiments, bipolar pulses, alternating pulses, bidirectional pulses, and reverse pulses mean the same. In some embodiments, negative current density pulses will be followed by positive current density pulses, without residing at a minimum. A pulse waveform including both negative and positive current density pulses will include a maximum value for negative pulses, a maximum value for positive pulses, and the values do not have to be the same. Further, in some embodiments, the duration of negative current density pulse does not have to be the same duration of a positive current density pulse.

In some embodiments, the duration of pulses does not have to be the same duration, regardless whether the pulses are negative or positive.

In some embodiments, a pulse waveform can combine two or more pulse waveforms concurrently or alternatively. In some embodiments, a pulse waveform can include negative pulses, followed by positive pulses. Thus, having a maximum and minimum amplitude for the negative pulses and a maximum and a minimum amplitude for the positive pulses.

While FIG. 3 depicts certain current density values of the maximum and minimum pulse amplitudes and pulse duration, it should be appreciated that the illustrated values are exemplary only. In some embodiments of the current waveform of FIG. 3, the average current density is controlled in pulses and each pulse maximum is controlled at most at 0.2 mA/cm$^2$ and the minimum amplitude is 0. In some embodiments of the current waveform of FIG. 3, the average current density is controlled in pulses and each pulse maximum is controlled at or below 0.5 mA/cm$^2$ and the minimum amplitude is 0. In some embodiments of the current waveform of FIG. 3, the average current density is controlled in pulses and each pulse maximum is controlled from 0.2 mA/cm$^2$ to 0.5 mA/cm$^2$ and the minimum amplitude is 0. In some embodiments of the current waveform of FIG. 3, the average current density is controlled in pulses and each pulse maximum is controlled from 0.01 mA/cm$^2$ to 10 mA/cm$^2$ and the minimum amplitude is 0. In some embodiments of the current waveform of FIG. 3, the average current density is controlled in pulses and each pulse maximum is controlled from 0.05 mA/cm$^2$ to 0.5 mA/cm$^2$ and the minimum amplitude is 0. In some embodiments of the current waveform of FIG. 3, the average current density is controlled in pulses and each pulse maximum is controlled at or below 0.2 mA/cm$^2$ and the minimum amplitude is 0. In some embodiments of the current waveform of FIG. 3, the average current density is controlled in pulses and each pulse maximum is controlled at 0.01, 0.05, 0.1, 0.15, 0.2, 0.25, 0.3, 0.35, 0.4, 0.45, 0.5 mA/cm$^2$ or in the range between any two values serving as endpoints. In some embodiments, the current density is given as the root-mean-square (rms). In some embodiments, the current density is given as the average current density. In some embodiments, the current density can be given as the peak current density, which can be as high as 1 mA/cm$^2$ or 2 mA/cm$^2$ with a duty cycle of 50% and 25%, respectively.

In some embodiments, the pulse has a positive constant slope (other than vertical) to the maximum amplitude, followed by a duration at the constant maximum amplitude, followed by a negative constant slope (other than vertical) to 0, followed by a duration at 0. In some embodiments, the minimum can be other than 0. In some embodiments, the slope can be other than constant, such as exponential. In some embodiments of the current waveform of FIG. 3, the pulses are not triangular. In some embodiments of FIG. 3, the pulses are a square wave, wherein the maximum and the minimum amplitudes are of the same duration or not. In some embodiments of the current waveform of FIG. 3, the pulses are not square wave. In some embodiments, the pulse wave is sinusoidal, non-sinusoidal, or any combination. In some embodiments, the pulse wave is periodic square wave, rectangular wave, saw tooth wave, spiked wave, trapezoidal wave, triangle wave, or combinations thereof.

In some embodiments of FIG. 3, the duration of the maximum amplitude of the pulses is less than the duration of the minimum amplitude between pulses. In some embodiments of FIG. 3, the pulse duration (or width) is defined as the time between the minimums with a maximum (either positive or negative) between the two minimums. In some embodiments, the pulse duration (or width) is given in units of time. In some embodiments, the pulse duration (or width) ranges from 50 microseconds to 1 milliseconds. In some embodiments, the pulse duration (or width) ranges from 200 microseconds to 300 microseconds. In some embodiments, the pulse duration (or width) ranges from 10 microseconds to 500 microseconds. In some embodiments, the pulse duration (or width) ranges from 50 microseconds to 5 milliseconds. In some embodiments, the pulse duration (or width) is less than 50 microseconds or greater than 5 milliseconds. In some embodiments, the pulse duration (or width) is 500 microseconds. In some embodiments of FIG. 3, the duration of the maximum amplitude of the pulses is greater than the duration of the minimum amplitude between pulses. In some embodiments of the current waveform of FIG. 3, the minimum amplitude is 0 mA/cm$^2$. In some embodiments of FIG. 3, the minimum amplitude is greater than 0 mA/cm$^2$ (meaning "more" negative than 0 with respect to FIG. 3). In some embodiments of the current waveform of FIG. 3, the maximum (and minimum) amplitude can increase from pulse to pulse. In some embodiments of the current waveform of FIG. 3, the maximum (and minimum) amplitude can decrease from pulse to pulse. In some embodiments of the current waveform of FIG. 3, the maximum (and minimum) amplitude can increase from pulse to pulse, and then decrease from pulse to pulse, and repeat.

In some embodiments of the current waveform of FIG. 3, the average current density is controlled in pulses at any of the above values and the rate of pulses is from 100 hertz to 300 hertz. In some embodiments of the current waveform of FIG. 3, the average current density is controlled in pulses at any of the above values and the rate of pulses is from 1 hertz to 200 hertz. In some embodiments, the pulse is less than 1 hertz. In some embodiments of the current waveform of FIG. 3, the average current density is controlled in pulses at any of the above values and the rate of pulses is from 1 hertz to 500 hertz. In some embodiments of the current waveform of FIG. 3, the average current density is controlled in pulses at any of the above values and the rate of pulses is 200 hertz. In some embodiments of the current waveform of FIG. 3, the average current density is controlled in pulses at any of the above values and the rate of pulses is from 10 hertz to 500 hertz. In some embodiments of the current waveform of FIG. 3, the average current density is controlled in pulses wherein the rate of pulses is from 1 hertz to 500 hertz, or any value in between in increments of 1 hertz.

In some of the embodiments of FIG. 3, a pulse wave travels in wave packets (or wave trains). In some embodiments, the wave packets are defined by the number of pulses, the duration or width of pulses in the packet, the average current density of pulses, the duty cycle of pulses in the wave packet, and the frequency of the wave packets. In some embodiments, the wave packet can have from 2 pulses or greater with or without alternating polarity. In some embodiments of FIG. 3, the wave packet can have from 2 pulses to 20 pulses with or without alternating polarity. In some embodiments of FIG. 3, the wave packets can be generated at a frequency from 10 Hertz or greater. In some embodiments of FIG. 3, the wave packets can be generated at a frequency from 10 Hertz to 500 Hertz. In some embodiments, the duty cycle of the pulses in the wave packets ranges from 1% to 90%.

In some embodiments, the pulses have an average current density of 0.01 mA/cm$^2$ to 10 mA/cm$^2$.

In some embodiments of the current waveform of FIG. 3, the iontophoresis treatment is applied for a duration of from 1 minute to 5 minutes. In some embodiments of the current waveform of FIG. 3, the iontophoresis treatment is applied for a duration (in minutes) of 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, 60, or any range between any two values serving as endpoints. In some embodiments of the current waveform of FIG. 3, the first electrode 114 has negative polarity and the second electrode 116 has positive polarity when the pulses extend below 0. However, the first electrode 114 is positive and the second electrode 116 is negative when the pulses extend above 0. Thus, indicating a reversal in the direction of current.

Referring to FIG. 4, a third current density waveform is illustrated for iontophoresis. FIG. 4 illustrates one embodiment of a waveform that can be generated by the iontophoresis device of FIG. 1. FIG. 4 shows a continuous direct current concurrent with a pulse wave. The current density waveform is controlled in negative unipolar pulses and between pulses, the current density is controlled as continuous direct current. Stated another way, the current waveform of FIG. 4 can be described as the combination between a direct current and a bidirectional pulse taken as an offset direct current with a duty cycle smaller than 100%. The two waveforms are applied concurrently for the duration or any part of the iontophoresis treatment. Specifically, the pulse wave has an on and off period. The superposition of the pulse wave on top of continuous direct current causes the current profile to show the pulse beginning at the constant value of the direct current. The pulse reaches a maximum for the predetermined duration and then the profile goes to 0. After the off period from the 0 value, the continuous direct current is applied until then next pulse. Thus, the current density of the waveform can be described as the addition of continuous direct current of a first amplitude with a pulse of a second amplitude, wherein the pulse has an off period before applying the direct current again. A pulse is counted starting from the direct current amplitude, reaching the maximum pulse amplitude, and then returning to the minimum amplitude or 0. Thus, a pulse does not include the period of the minimum amplitude at 0. A pulse cycle does include the period at the minimum amplitude. In some embodiments, the durations of the maximum and minimum amplitudes are the same.

In some embodiments, the pulse is expressed to have a % duty cycle. In some embodiments, expressing a % duty cycle with respect to a pulse wave means that the electrical current is on for the % duty cycle. For example, 50% duty cycle of pulses means electrical current is on for 50% and off for 50% of the pulse cycle, 30% duty cycle of pulses means electrical current is on for 30% and off for 70% of the pulse cycle. In some embodiments, the % duty cycle of unidirectional pulses is 5, 10, 15, 20, 25, 30, 35, 40, 45, 50, 55, 60, 65, 70, 75, 80, 85, 90, 95, or any range between any two values serving as endpoints. In some embodiments, the % duty cycle of a respective bipolar pulse is 0.01, 5, 10, 15, 20, 25, 30, 35, 40, 45, 50, 55, 60, 65, 70, 75, 80, 85, 90, 95, 100 or any range between any two values serving as endpoints. In some embodiments, the duty cycle of pulses ranges from 1% to 90%. In some embodiments, the pulse, meaning the "on" period can be expressed as a duration. In some embodiments, the pulse "off" period can be expressed as a duration. In some embodiments, the pulse wave is expressed in hertz, meaning cycles per second. In some embodiments, the pulses can be reversed by alternating the polarities of the first and second electrodes between negative and positive. In some embodiments, bipolar pulses, alternating pulses, bidirectional pulses, and reverse pulses mean the same. In some embodiments, negative current density pulses will be followed by positive current density pulses, without residing at a minimum. A pulse waveform including both negative and positive current density pulses will include a maximum value for negative pulses, a maximum value for positive pulses, and the values do not have to be the same. Further, in some embodiments, the duration of negative current density pulse does not have to be the same duration of a positive current density pulse. In some embodiments, the duration of pulses does not have to be the same duration, regardless whether the pulses are negative or positive.

In some embodiments, a pulse waveform can combine two or more pulse waveforms concurrently or alternatively. In some embodiments, a pulse waveform can include negative pulses, followed by positive pulses. Thus, having a maximum and minimum amplitude for the negative pulses and a maximum and a minimum amplitude for the positive pulses.

While FIG. 4 depicts certain current density values of the maximum and minimum pulse amplitudes and pulse duration, it should be appreciated that the illustrated values are exemplary only. In some embodiments of the current waveform of FIG. 4, concurrent with a direct current, the average current density is controlled in pulses and each pulse maximum is controlled at most at 0.2 mA/cm$^2$ and the minimum amplitude is 0. This means that the addition of the pulse to the direct current totals 0.4 mA/cm$^2$. In some embodiments of the current waveform of FIG. 4, concurrent with a direct current, the average current density is controlled in pulses and each pulse maximum is at or below 0.5 mA/cm$^2$ and the minimum amplitude is 0, and direct current average current density is controlled at or below an average of 0.5 mA/cm$^2$. In some embodiments of the current waveform of FIG. 4, concurrent with a direct current, the average current density is controlled in pulses and each pulse maximum is controlled from 0.2 mA/cm$^2$ to 0.5 mA/cm$^2$ and the minimum amplitude is 0, and the direct current average current density is controlled from 0.2 mA/cm$^2$ to 0.5 mA/cm$^2$. In some embodiments of the current waveform of FIG. 4, concurrent with a direct current, the average current density is controlled in pulses and each pulse maximum is controlled at or below 0.2 mA/cm$^2$ and the minimum amplitude is 0, and the direct current average current density is controlled at or below 0.2 mA/cm$^2$. In some embodiments of the current waveform of FIG. 4, concurrent with direct current, the average current density is controlled in pulses and each pulse maximum is controlled from 0.01 mA/cm$^2$ to 10 mA/cm$^2$, and the direct current average current density is controlled from 0.01 mA/cm$^2$ to 0.5 mA/cm$^2$, In some embodiments of the current waveform of FIG. 4, concurrent with direct current, the average current density is controlled in pulses and the direct current and each pulse maximum is controlled on average at 0.01, 0.05, 0.1, 0.15, 0.2, 0.25, 0.3, 0.35, 0.4, 0.45, 0.5 mA/cm$^2$ or in the range between any two values serving as endpoints. In some embodiments, the current density is given as the root-mean-square (rms). In some embodiments, the current density is given as the average current density. In some embodiments, the current density can be given as the peak current density, which can be as high as 1 mA/cm² or 2 mA/cm² with a duty cycle of 50% and 25%, respectively.

In some embodiments of FIG. 4, the pulses are triangular with a defined maximum and minimum, wherein the maximum and the minimum amplitudes are of the same duration. Specifically, the pulse has a positive constant slope (other than vertical) to the maximum amplitude, followed by a period at the constant maximum amplitude, followed by a negative constant slope (other than vertical) to 0, followed by a period at 0. In some embodiments, the minimum can be other than 0. In some embodiments, the slope can be other than constant, such as exponential. In some embodiments, the pulse wave is sinusoidal, non-sinusoidal, or any combination. In some embodiments, the pulse wave is periodic square wave, rectangular wave, saw tooth wave, spiked wave, trapezoidal wave, triangle wave, or combinations thereof.

In some embodiments of FIG. 4, the duration of the maximum amplitude of the pulses is less than the duration of the minimum amplitude between pulses. In some embodiments of FIG. 4, the pulse duration (or width) is defined as the time between the minimums with a maximum (either positive or negative) between the two minimums. In some embodiments, the pulse duration (or width) is given in units of time. In some embodiments, the pulse duration (or width) ranges from 50 microseconds to 1 milliseconds. In some embodiments, the pulse duration (or width) ranges from 200 microseconds to 300 microseconds. In some embodiments, the pulse duration (or width) ranges from 10 microseconds to 500 microseconds. In some embodiments, the pulse duration (or width) ranges from 50 microseconds to 5 milliseconds. In some embodiments, the pulse duration (or width) is less than 50 microseconds or greater than 5 milliseconds. In some embodiments, the pulse duration (or width) is 500 microseconds. In some embodiments of FIG. 4, the duration of the maximum amplitude of the pulses is greater than the duration of the minimum amplitude between pulses. In some embodiments of the current waveform of FIG. 4, the minimum amplitude is 0 mA/cm². In some embodiments of FIG. 4, the minimum amplitude is greater than 0 mA/cm² (meaning "more" negative than 0 with respect to FIG. 4). In some embodiments of the current waveform of FIG. 3, the maximum (and minimum) amplitude can increase from pulse to pulse. In some embodiments of the current waveform of FIG. 4, the maximum (and minimum) amplitude can decrease from pulse to pulse. In some embodiments of the current waveform of FIG. 4, the maximum (and minimum) amplitude can increase from pulse to pulse, and then decrease from pulse to pulse, and repeat.

In some embodiments of the current waveform of FIG. 4, the average current density is controlled as direct current concurrently with pulses at any of the above values and the rate of pulses is from 100 hertz to 300 hertz. In some embodiments of the current waveform of FIG. 4, the current density is controlled as direct current concurrently with pulses at any of the above values and the rate of pulses is from 1 hertz to 500 hertz. In some embodiments of the current waveform of FIG. 4, the average current density is controlled as direct current concurrently with pulses wherein the rate of pulses is from 1 hertz to 500 hertz, or any value in between in increments of 1 hertz. In some embodiments of the current waveform of FIG. 4, concurrent with direct current, the average current density is controlled in pulses at any of the above values and the rate of pulses is from 10 hertz to 500 hertz. In some embodiments of the current waveform of FIG. 4, each pulse has a duration of between 0.001 seconds to 1 second or any value in between. In some embodiments of the current waveform of FIG. 4, concurrent with direct current, the average current density is controlled in pulses and the rate of pulses is 200 hertz and each pulse has a duration of 500 microseconds.

In some of the embodiments of FIG. 4, the pulses are applied as a wave packet (or wave train). In some embodiments, the wave packets are defined by the number of pulses, the duration or width of pulses in the packet, the average current density of pulses, the duty cycle of pulses in the wave packet, and the frequency of the wave packets. In some embodiments, the wave packet can have from 2 pulses or greater with or without alternating polarity. In some embodiments of FIG. 4, the wave packet can have from 2 pulses to 20 pulses with or without alternating polarity. In some embodiments of FIG. 4, the wave packets can be generated at a frequency from 10 Hertz or greater. In some embodiments of FIG. 4, the wave packets can be generated at a frequency from 10 Hertz to 500 Hertz. In some embodiments, the duty cycle of the pulses in the wave packets ranges from 1% to 90%. In some embodiments, the pulses of wave packets have an average current density of 0.01 mA/cm² to 10 mA/cm².

In some embodiments of the current waveform of FIG. 4, the iontophoresis treatment is applied for a duration (in minutes) of 1, 1.5, 2, 2.5, 3, 3.5, 4, 4.5, 5 or any range between any two values serving as endpoints. In some embodiments of the waveform of FIG. 4, the electrical current is applied as continuous direct current and in pulses for a duration (in minutes) of 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, 60, or any range between any two values serving as endpoints. In some embodiments of the current waveform of FIG. 4, the pulses are unipolar pulses. In some embodiments of the current waveform of FIG. 4, the first electrode 114 has negative polarity and the second electrode 116 has positive polarity when the pulses extend below 0. However, the first electrode 114 is positive and the second electrode 116 is negative when the pulses extend above 0. Thus, indicating a reversal in the direction of current.

In some embodiments, the current waveforms of FIGS. 2, 3 and 4 can be combined to provide concurrent waveforms for the administration of aqueous active agent compositions, such as vitamin C compositions, into the skin via the use of iontophoresis. In some embodiments, the current waveforms of FIGS. 2, 3 and 4 can be combined to provide concurrent waveforms for the administration of one or more of a face care or body care composition, comprising, in particular, an active agent chosen from humectant or moisturizing active agents, anti-ageing active agents, for example depigmenting active agents, active agents that act on cutaneous microcirculation, or seboregulating active agents, a composition for making up the face or body, a hair composition, in particular, a composition for washing the hair, for hair care or conditioning, for temporary form retention or shaping of the hair, for the temporary, semi-permanent or permanent dyeing of the hair, or for relaxing or permanent waving, in particular, a composition for relaxing, dyeing or bleaching the roots and hair, and a composition for the scalp, in particular, an antidandruff composition, a composition for preventing hair loss or for promoting regrowth of the hair, an anti-seborrheic composition, an anti-inflammatory composition, an anti-irritation or soothing composition, a mark-preventing composition or a composition for stimulating or protecting the scalp.

In some embodiments, the current waveforms of FIGS. 2, 3 and 4 can be combined to provide combinations of waveforms that are generated by the circuitry of the iontophoresis device of FIG. 1. In some embodiments, the current waveform of any FIG. 2-4 is applied for a first duration, followed by a different current waveform of any FIG. 2-4 for a second duration or vice versa. In some embodiments two or more different current waveforms can be cycled for the entire electrical current treatment duration. The particulars of the waveform as described above for FIGS. 2-4 are similarly applicable to combined treatments applying the two or more different waveforms. That is, any one or more of the embodiments of the direct current waveform can be combined with any one or more of the pulse waveforms in sequence or simultaneously.

In the case of the waveforms of FIGS. 2, 3, and 4, the peak voltage at maximum peak is 99 volts. In some embodiments, the maximum duration of conducting electrical current is 120 minutes during the iontophoresis treatment.

Every embodiment of the current density waveforms described in connection with FIGS. 2, 3 and 4 and the combination of waveforms can be used for iontophoresis of every embodiment of the compositions.

Figure 6:
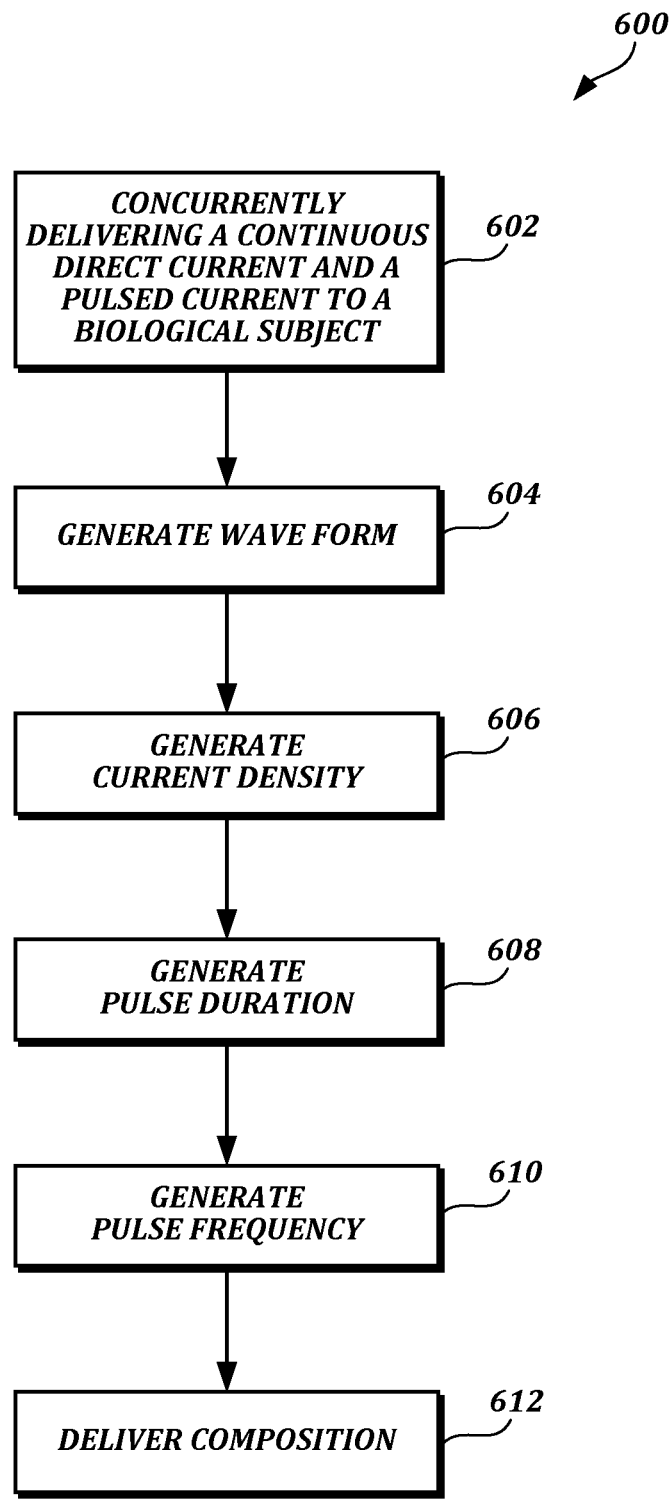
FIG. 6 is a flow diagram of a method in accordance with one embodiment.

FIG. 6 illustrates embodiments of a method 600 for delivering a cosmetic composition through the generation of electrical stimuli of certain waveform types. In some embodiments, the method includes a step 602 for concurrently delivering a continuous direct current and a pulsed current to a biological subject, the continuous direct current and the pulsed current is of a character and for a duration sufficient to deliver a cosmetic composition to the biological subject.

In some embodiments, the illustrated steps 604, 606, 608, and 610 are optional. Further, in some embodiments, the sequence of the steps 604, 606, 608, and 610 can be in any order and is not confined to the illustration. In some embodiments, the method 600 includes a step 604 for generating waveforms. In some embodiments, the user makes selections that cause the iontophoresis device to generate the selected waveform or waveforms that constitute the electrical stimuli. In some embodiments, the method 600 includes a step 606 for generating current density. In some embodiments, the user makes selections that cause the iontophoresis device to generate the selected current density. In some embodiments, the method 600 includes a step 608 for generating pulse duration. In some embodiments, the user makes selections that cause the iontophoresis device to generate the selected pulse duration. In some embodiments, the method 600 includes a step 610 for generating pulse frequency. In some embodiments, the user makes selections that cause the iontophoresis device to generate the selected pulse frequency.

In some embodiments, the method 600 for concurrently delivering the continuous direct current and the pulsed current to a biological subject includes generating a continuous direct current stimulus having an average current density ranging from 0.01 mA/cm$^2$ to 0.5 mA/cm$^2$.

In some embodiments, the method 600 for concurrently delivering the continuous direct current and the pulsed current to a biological subject includes generating a continuous direct current stimulus having an average current density of 0.2 mA/cm$^2$.

In some embodiments, the method 600 for concurrently delivering the continuous direct current and the pulsed current to a biological subject includes generating a pulsed current stimulus having an average current density ranging from 0.01 mA/cm$^2$ to 10 mA/cm$^2$, a pulse duration ranging from 50 microseconds to 1 milliseconds, and a pulse frequency ranging from 10 Hertz to 500 Hertz, and a duty cycle of pulses ranging from 1% to 90%.

In some embodiments, the method 600 for concurrently delivering the continuous direct current and the pulsed current to a biological subject includes generating a pulsed alternating current stimulus having an average current density of 0.2 mA/cm$^2$, a pulse duration of 500 microseconds, and a pulse frequency of 200 Hertz.

In some embodiments, the method 600 for concurrently delivering the continuous direct current and the pulsed current to a biological subject includes generating a pulsed current having an average current density ranging from 0.01 mA/cm$^2$ to 10 mA/cm$^2$, a pulse width ranging from 50 microseconds to 1 milliseconds, at least one wave packet (or wave train) ranging from 2 to 20 pulses, a frequency of wave packets ranging from 10 Hertz to 500 Hertz, and a duty of pulses ranging from 1% to 90%.

In some embodiments, the method 600 for concurrently delivering the continuous direct current and the pulsed current to a biological subject includes generating a pulsed current stimulus having an average current density ranging from 0.01 mA/cm$^2$ to 10 mA/cm$^2$, a pulse width ranging from 50 microseconds to 1 milliseconds, at least one wave packet (wave train) having from 2 to 20 pulses with alternating polarity, a frequency of wave packets ranging from 10 Hertz to 500 Hertz, and a duty cycle of pulses ranging from 1% to 90%.

In some embodiments, the method 600 for concurrently delivering the continuous direct current and the pulsed current to a biological subject includes generating a pulsed current having sinusoidal waveforms, non-sinusoidal waveforms, or combinations thereof.

In some embodiments, the method 600 for concurrently delivering the continuous direct current and the pulsed current to a biological subject includes generating a pulsed current having periodic square waveforms, rectangular waveforms, saw tooth waveforms, spiked waveforms, trapezoidal waveforms, triangle waveforms, or combinations thereof.

In some embodiments, the method 600 comprises delivering a cosmetic composition chosen from a face care or body care composition, comprising in particular, an active agent chosen from humectant or moisturizing active agents, anti-ageing active agents, for example depigmenting active agents, active agents that act on cutaneous microcirculation, or seboregulating active agents, or a composition for making up the face or body.

Figure 7:
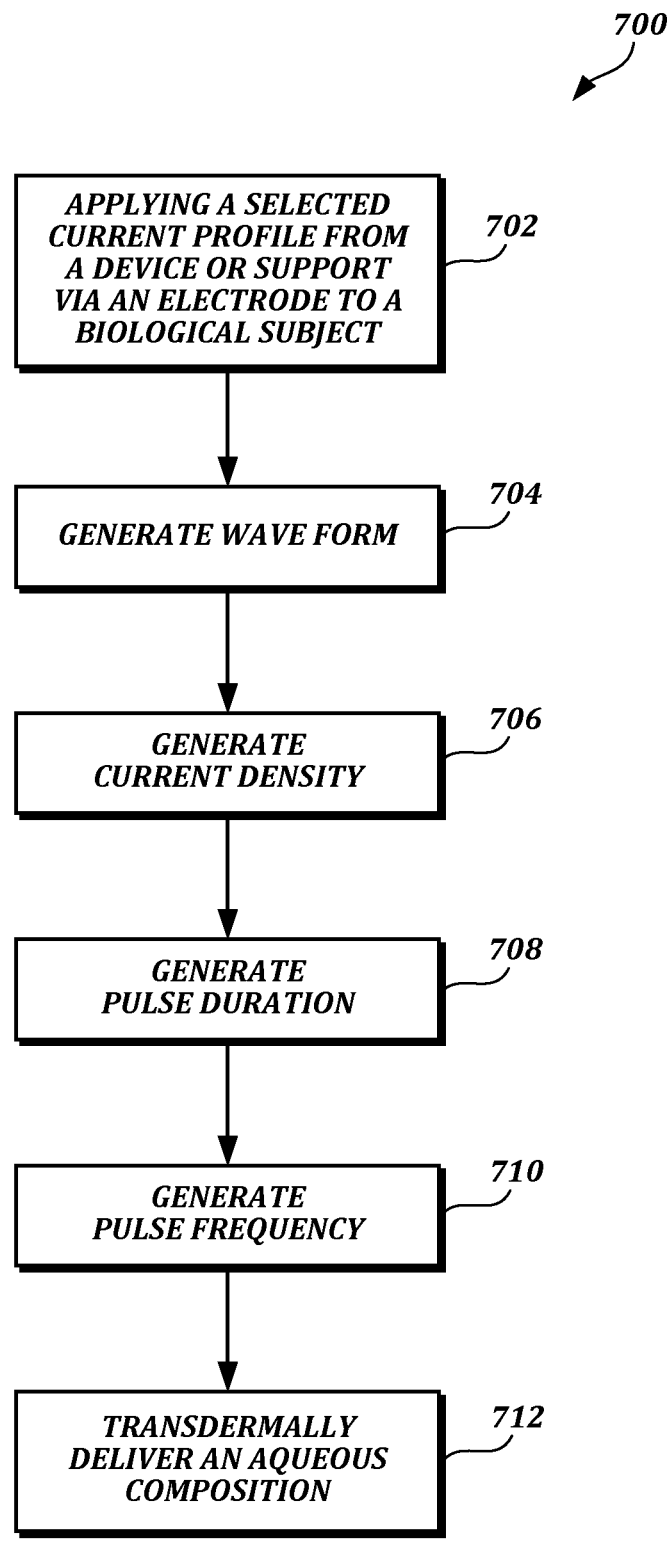
FIG. 7 is a flow diagram of a method in accordance with one embodiment.

FIG. 7 illustrates embodiments of a method 700 for delivering an aqueous active agent composition, such as an aqueous vitamin C composition through the skin to a biological subject through the generation of electrical stimuli of certain waveform types.

In some embodiments, the method 700 includes step 702 for applying a selected current profile, either continuous direct current, pulsed current or a combination of both, from any device and/or support comprising at least one electrode to a biological subject, the continuous direct current, the pulsed current or the combination of both is of a character and for a duration sufficient to transdermally deliver an aqueous composition to a biological subject, thus, transporting different rates of vitamin C across the skin in accordance to the selected current mode.

In some embodiments, the illustrated steps 704, 706, 708, and 710 are optional. Further, in some embodiments, the sequence of the steps 704, 706, 708, and 710 can be in any order and is not confined to the illustration. In some embodiments, the method 700 includes a step 704 for generating waveforms. In some embodiments, the user makes selections that cause the iontophoresis device to generate the selected waveform or waveforms that constitute the electrical stimuli. In some embodiments, the method 700 includes a step 706 for generating current density. In some embodiments, the user makes selections that cause the iontophoresis device to generate the selected current density. In some embodiments, the method 700 includes a step 708 for generating pulse duration. In some embodiments, the user makes selections that cause the iontophoresis device to generate the selected pulse duration. In some embodiments, the method 700 includes a step 710 for generating pulse frequency. In some embodiments, the user makes selections that cause the iontophoresis device to generate the selected pulse frequency. In step 712, the method 700 includes transdermally delivering an aqueous composition.

In some embodiments of the method 700 of delivering an aqueous vitamin C composition through the skin, applying a selected current profile to a biological subject includes generating a continuous direct current stimulus having an average current density ranging from 0.01 mA/cm$^2$ to 0.5 mA/cm$^2$.

In some embodiments of the method 700 of delivering an aqueous vitamin C composition through the skin, applying a selected current profile to a biological subject includes generating a continuous direct current stimulus having an average current density of 0.2 mA/cm$^2$.

In some embodiments of the method 700 of delivering an aqueous vitamin C composition through the skin, applying a selected current profile to a biological subject includes generating a pulsed current having sinusoidal waveforms, non-sinusoidal waveforms, or combinations thereof.

In some embodiments of the method 700 of delivering an aqueous vitamin C composition through the skin, applying a selected current profile to a biological subject includes generating a pulsed current having periodic square waveforms, rectangular waveforms, saw tooth waveforms, spiked waveforms, trapezoidal waveforms, triangle waveforms, or combinations thereof.

In some embodiments of the method 700 of delivering an aqueous vitamin C composition through the skin, applying a selected current profile to a biological subject includes concurrently delivering the continuous direct current and the pulsed current and generating a pulsed current stimulus having an average current density ranging from 0.05 mA/cm$^2$ to 0.5 mA/cm$^2$; a pulse duration ranging from 200 microseconds to 300 microseconds; and a pulse frequency ranging from 100 Hertz to 300 Hertz.

In some embodiments, the method 700 of delivering an aqueous vitamin C composition through the skin further comprises transdermally delivering an aqueous composition including, one or more of vitamin C, vitamin C derivatives, ions of vitamin C, and ions of vitamin C derivatives present in amounts ranging from 0.1% to 20% by weight; one or more silicon surface-active agents present in amounts ranging from 0.01% to 30% by weight; one or more ionic polymers present in amounts ranging from 0.01% to 10% by weight; and water present in an amount of at least 30% by weight.

In some embodiments, the method 700 of delivering an aqueous vitamin C composition through the skin, further comprises transdermally delivering an aqueous composition including, one or more of vitamin C, vitamin C derivatives, ions of vitamin C, and ions of vitamin C derivatives present in amounts ranging from 0.01% to 30% by weight; one or more silicon surface-active agents present in amounts ranging from 0.01% to 30% by weight; one or more non-ionic polymers present in amounts ranging from 0.01% to 20% by weight; and water present in an amount of at least 30% by weight.

In some embodiments of the method 700 of delivering an aqueous vitamin C composition through the skin, transdermally delivering the aqueous active agent composition includes generating a continuous direct current stimulus having an average current density ranging from 0.01 mA/cm$^2$ to 0.5 mA/cm$^2$; and generating a pulsed current stimulus having an average current density ranging from 0.01 mA/cm$^2$ to 10 mA/cm$^2$; a pulse duration ranging from 10 microseconds to 500 microseconds; and a pulse frequency ranging from 10 Hertz to 500 Hertz; the continuous direct current and the pulsed current of a duration sufficient to transdermally deliver an aqueous active agent composition to a biological subject.

An iontophoresis composition for use with the iontophoresis methods described above in relation to FIGS. 6 and 7 is disclosed.

In some embodiments, the iontophoresis composition includes one or more of vitamin C, vitamin C derivatives, ions of vitamin C, and ions of vitamin C derivatives present in amounts ranging from 0.1% to 30% by weight; one or more silicon materials present in amounts ranging from 0.1% to 30% by weight; and water present in an amount of at least 20% by weight; the iontophoresis composition having an aqueous phase that is at least 30% by weight relative to the total weight of the iontophoresis composition.

In some embodiments, the iontophoresis composition further comprises one or more ionic polymers present in amounts ranging from 0.01% to 10% by weight; wherein the one or more of vitamin C, vitamin C derivatives, ions of vitamin C, and ions of vitamin C derivatives are present in amounts ranging from 0.1% to 30% by weight.

In some embodiments, the iontophoresis composition further comprises one or more non-ionic polymers present in amounts ranging from 0.01% to 20% by weight; wherein the one or more of vitamin C, vitamin C derivatives, ions of vitamin C, and ions of vitamin C derivatives are present in amounts ranging from 0.01% to 30% by weight. In some embodiments, the iontophoresis composition further comprises a pH ranging from 2 to 7.5.

In some embodiments of the iontophoresis composition, the one or more silicon materials include one or more silicon surface-active agents. In some embodiments of an iontophoresis composition, the silicon-containing surface active agents are selected from polydimethylsiloxane, poly[oxy(dimethylsilylane)], polyvinyl siloxane, cyclohexasiloxane, derivatives thereof, or any combination thereof.

In some embodiments of the iontophoresis composition, the ionic polymers and nonionic polymers are selected from acrylonitrile/methyl methacrylate/vinylidene chloride copolymer, biosaccharide gum-1, sodium styrene/maleic anhydride copolymer, xanthan gum, ammonium polyacryloyldimethyl taurate, derivatives thereof, their ions, and any combination thereof.

In some embodiments of the iontophoresis composition, vitamin C derivatives are selected from ascorbyl palmitate and magnesium ascorbyl phosphate, ascorbyl tetraisopalmitoyl, tetrahexyldecyl ascorbate, sodium ascorbyl phosphate, and any combination thereof.

In some embodiments of the iontophoresis composition, the composition further comprises a vitamin, a fat, a solvent, a humectant, a viscosity reducer, a preservative, a chelating agent, a viscosity controller, a skin conditioner, an emollient, an emulsifier, a cleansing agent, an emulsion stabilizer, a viscosity increaser, an antioxidant, a binder, a skin bleaching agent, a pH adjuster, a buffering agent, a denaturant, a bulking agent, an opacifying agent.

In some embodiments of the iontophoresis composition, the composition includes ionic polymers and nonionic polymers selected from biosaccharide gum-1 (and) sodium levulinate (and) glyceryl caprylate (and) sodium anisate, acrylates/c10-30 alkyl acrylate crosspolymer, carbomer, sodium styrene/maleic anhydride copolymer, nylon-12, xanthan gum, derivatives thereof, their ions, or any combination thereof.

In some embodiments, the iontophoresis composition has a pH from 2 to 7.4.

In some embodiments, the iontophoresis composition has a pH from 2 to 7.

In some embodiments, the iontophoresis composition has a pH from 5.7 to 6.3.

In some embodiments, the iontophoresis composition has a pH from 2 to 6.3.

In some embodiments, the iontophoresis composition includes one or more vitamins selected from vitamin B5, vitamin A, vitamin B3, and vitamin E.

In some embodiments, the iontophoresis composition includes one or more fats selected from nut oils, seed oils, and plant oils.

In some embodiments, the iontophoresis composition includes one or more solvents selected from water, deionized water, and Eau de la Roche-Posay™.

In some embodiments, the iontophoresis composition includes one or more humectants selected from glycerin, caprylyl glycol, and sodium hyaluronate.

In some embodiments, the iontophoresis composition includes one or more viscosity reducers selected from glycerine.

In some embodiments, the iontophoresis composition includes one or more preservatives selected from phenoxyethanol, salicylic acid, and sodium methylparaben.

In some embodiments, the iontophoresis composition includes one or more chelating agents selected from disodium EDTA.

In some embodiments, the iontophoresis composition includes one or more viscosity controllers selected from disodium EDTA, ammonium polyacryldimethyltauramide, and nylon-12.

In some embodiments, the iontophoresis composition includes one or more skin conditioners selected from C12-15 alkyl benzoate, caprylyl glycol, glyceryl stearate and polyethylene glycol 100 Stearate, tocopheryl acetate, sodium hyaluronate, ethylhexyl palmitate, dimethicone and dimethiconol, dimethicone, dimethicone and dimethicone/vinyl dimethicone crosspolymer, biosaccharide gum-1, oxothiazolidinecarboxylic acid, ascorbic acid, sodium styrene/maleic anhydride copolymer, salicylic acid, cyclohexasiloxane, hydrogenated polyisobutene, biosaccharide gum-1 and sodium levulinate and glyceryl caprylate and sodium anisate, lemon extract, alcohol and *Gentiana lutea* root extract, and dimethicone and polyethylene glycol/polypropylene glycol-18/18 dimethicone.

In some embodiments, the iontophoresis composition includes one or more emollients selected from C12-15 alkyl benzoate, caprylyl glycol, glyceryl stearate and polyethylene glycol 100 Stearate, ethylhexyl palmitate, dimethicone and dimethiconol, dimethicone, dimethicone and dimethicone/vinyl dimethicone crosspolymer, cyclohexasiloxane, hydrogenated polyisobutene, biosaccharide gum-1 and sodium levulinate and glyceryl caprylate and sodium anisate, and dimethicone and polyethylene glycol/polypropylene glycol-18/18 dimethicone.

In some embodiments, the iontophoresis composition includes one or more emulsifiers selected from glyceryl stearate and polyethylene glycol 100 Stearate, cetyl alcohol, xanthan gum, triethanolamine, biosaccharide gum-1 and sodium levulinate and glyceryl caprylate and sodium anisate, and dimethicone and polyethylene glycol/polypropylene glycol-18/18 dimethicone.

In some embodiments, the iontophoresis composition includes one or more cleansing agents selected from glyceryl stearate and polyethylene glycol 100 Stearate.

In some embodiments, the iontophoresis composition includes one or more stabilizers selected from cetyl alcohol, xanthan gum, ammonium polyacryldimethyltauramide, sodium styrene/maleic anhydride copolymer, carbomer, and acrylates/C10-30 alkylacrylate crosspolymer.

In some embodiments, the iontophoresis composition includes one or more viscosity increasers selected from cetyl alcohol, xanthan gum, dimethicone and dimethicone/vinyl dimethicone crosspolymer, carbomer, and acrylates/C10-30 alkylacrylate crosspolymer.

In some embodiments, the iontophoresis composition includes one or more antioxidants selected from tocopheryl acetate, and ascorbic acid.

In some embodiments, the iontophoresis composition includes one or more binders selected from xanthan gum.

In some embodiments, the iontophoresis composition includes one or more skin bleaching agents selected from oxothiazolidinecarboxylic acid.

In some embodiments, the iontophoresis composition includes one or more pH adjusters selected from triethanolamine, potassium hydroxide, and sodium hydroxide.

In some embodiments, the iontophoresis composition includes one or more buffering agents selected from potassium hydroxide and hydroxyethylpiperazine ethane sulfonic acid, and sodium hydroxide.

In some embodiments, the iontophoresis composition includes one or more denaturants selected from sodium hydroxide.

In some embodiments, the iontophoresis composition includes one or more bulking agents selected from nylon-12.

In some embodiments, the iontophoresis composition includes one or more opacifying agents selected from nylon-12.

The following are representative components of an 10% by weight vitamin C composition (10% vitamin C formula 1) suitable for use with all the embodiments of current waveforms in iontophoresis treatments. The amounts are given in weight percents. The component names follow the International Nomenclature of Cosmetic Ingredients (INCI US).

Water (a solvent): 43.525% (range of 30% to 50%, and any value in between); Glycerine (a humectant and viscosity reducer): 3% (range of 0% to 6%, and any value in between);

Phenoxyethanol (a preservative): 0.4% (range of 0% to 1%, and any value in between);

Disodium EDTA (a chelating agent and viscosity controller): 0.05% (range of 0% to 1%, and any value in between);

C12-15 alkyl benzoate (a skin conditioner and emollient): 3% (range of 0% to 6%, and any value in between);

Caprylyl glycol (a skin conditioner, emollient, and humectant): 0.3% (range of 0% to 1%, and any value in between);

Glyceryl Stearate and polyethylene glycol 100 Stearate (a skin conditioner, emollient, emulsifier, and cleansing agent): 2.5% (range of 0% to 5%, and any value in between);

Cetyl alcohol (a stabilizer, emulsifier, and viscosity increaser): 2% (range of 0% to 4%, and any value in between);

Tocopheryl acetate (an antioxidant and skin conditioner): 0.5% (range of 0% to 1%, and any value in between);

Xanthan gum (a binder, stabilizer, emulsifier, and viscosity increaser): 0.25% (range of 0% to 1%, and any value in between);

Sodium hyaluronate (a humectant and skin conditioner): 0.05% (range of 0% to 1%, and any value in between);

Ammonium polyacryldimethyltauramide (a stabilizer and viscosity controller): 0.8% (range of 0% to 2%, and any value in between);

Ethylhexyl palmitate (a skin conditioner and emollient): 3% (range of 0% to 6%, and any value in between);

Dimethicone and dimethiconol (a skin conditioner and emollient): 0.5% (range of 0% to 1%, and any value in between);

Dimethicone (a skin conditioner and emollient): 1% (range of 0% to 2%, and any value in between);

Dimethicone and dimethicone/vinyl dimethicone crosspolymer (a skin conditioner, emollient and viscosity increaser): 3% (range of 0% to 6%, and any value in between); Biosaccharide gum-1 (a skin conditioner): 3.4% (range of 0% to 7%, and any value in between);

Eau de la Roche-Posay™ (a water solvent): 1% (range of 0% to 2%, and any value in between);

Deionized water (a solvent): 2% (range of 0% to 4%, and any value in between);

Oxothiazolidinecarboxylic acid (skin bleaching agent and skin conditioner): 0.15% (range of 0% to 1%, and any value in between);

Triethanolamine (an emulsifier and pH adjuster): 0.15% (range of 0% to 1%, and any value in between);

Ascorbic Acid (vitamin C) (an antioxidant and skin conditioner): 10% (range of 0.1% to 25%, and any value in between);

Potassium hydroxide (a buffering agent and pH adjuster): 5.9% (range of 0% to 12%, and any value in between);

Sodium styrene/maleic anhydride copolymer (a stabilizer and skin conditioner): 3.125% (range of 0% to 7%, and any value in between);

Acrylonitrile/methyl methacrylate/vinylidene chloride copolymer (a charged polymer): 0.3% (range of 0% to 1%, and any value in between);

Fragrance: 0.1% (range of 0% to 1%, and any value in between);

pH 5.7 to 6.3 and any value in between.

The following are representative components of an 5% by weight vitamin C composition (5% vitamin C formula 2) suitable for use with all the embodiments of current waveforms in iontophoresis treatments. The amounts are given in weight percents. The component names follow the International Nomenclature of Cosmetic Ingredients (INCI US).

Water (a solvent): 40% (range of 30% to 50%, and any value in between);

Glycerine (a humectant and viscosity reducer): 7% (range of 0% to 14%, and any value in between);

Disodium EDTA (a chelating agent and viscosity controller): 0.05% (range of 0% to 1%, and any value in between);

Salicylic acid (a skin conditioner and preservative): 0.2% (range of 0% to 1%, and any value in between);

Sodium Methylparaben (a preservative): 0.2% (range of 0% to 1%, and any value in between);

Phenoxyethanol (a preservative): 0.7% (range of 0% to 2%, and any value in between);

Hydroxyethylpiperazine ethane sulfonic acid (a buffering agent): 0.5% (range of 0% to 1%, and any value in between);

Deionized water (a solvent): 29.517% (range of 20% to 40%, and any value in between);

Xanthan gum (a binder, stabilizer, emulsifier, and viscosity increaser): 0.2% (range of 0% to 1%, and any value in between);

Cyclohexasiloxane (an emollient and skin conditioner): 3% (range of 0% to 6%, and any value in between);

Hydrogenated polyisobutene (an emollient and skin conditioner): 4% (range of 0% to 8%, and any value in between);

Tocopheryl acetate (an antioxidant and skin conditioner): 0.5% (range of 0% to 1%, and any value in between);

Fragrance: 0.5% (range of 0% to 1%, and any value in between); Carbomer (a stabilizer and viscosity increaser): 0.8% (range of 0% to 2%, and any value in between);

Acrylates/C10-30 alkyl acrylate crosspolymer (a stabilizer and viscosity increaser): 0.4% (range of 0% to 1%, and any value in between);

Sodium hydroxide (a denaturant, pH adjuster, and buffering agent): 0.6% (range of 0% to 2%, and any value in between);

Deionized water (a solvent): 1.323% (range of 0% to 3%, and any value in between);

Biosaccharide gum-1 and sodium levulinate and glyceryl caprylate and sodium anisate (skin conditioners, emollients, emulsifiers): 3% (range of 0% to 6%, and any value in between);

Lemon extract (a skin conditioner and fragrance): 0.05% (range of 0% to 1%, and any value in between);

Alcohol and *Gentiana lutea* root extract (a skin conditioner and fragrance): 0.1% (range of 0% to 1%, and any value in between);

Dimethicone and polyethylene glycol/polypropylene glycol-18/18 Dimethicone (a skin conditioner, emollient, and emulsifier): 1.5% (range of 0% to 3%, and any value in between);

Nylon-12 (a bulking agent, opacifying agent, and viscosity controller): 0.5% (range of 0% to 1%, and any value in between);

Deionized water (a solvent): 15% (range of 0% to 30%, and any value in between);

Ascorbic Acid (vitamin C) (an antioxidant and skin conditioner): 5% (range of 0.1% to 25%, and any value in between);

Potassium hydroxide (a buffering agent and pH adjuster): 2.86% (range of 0% to 6%, and any value in between);

Sodium styrene/maleic anhydride copolymer (a stabilizer and skin conditioner): 2.5% (range of 0% to 5%, and any value in between);

pH 6.4 to 7.0 and any value in between.

In some embodiments, a vitamin C composition herein can "comprise" the specified components, leaving open the possibility of other unspecified components.

In some embodiments, a vitamin C composition herein can "consist" of the specific components, meaning the composition only includes the specified components. Stated another way, the specified components constitute 100% by weight of the vitamin C composition.

EXAMPLES

Iontophoretic transport experiments were conducted to quantify skin deposition of ascorbic acid (vitamin C) from two formulations (containing 5% (5% vitamin C formula 2) and 10% (10% vitamin C formula 1) of the active ingredient) at an iontophoretic current density of 0.2 mA/cm$^2$ (negative polarity at the active electrode) and a treatment application of 5 minutes.

Figure 5:
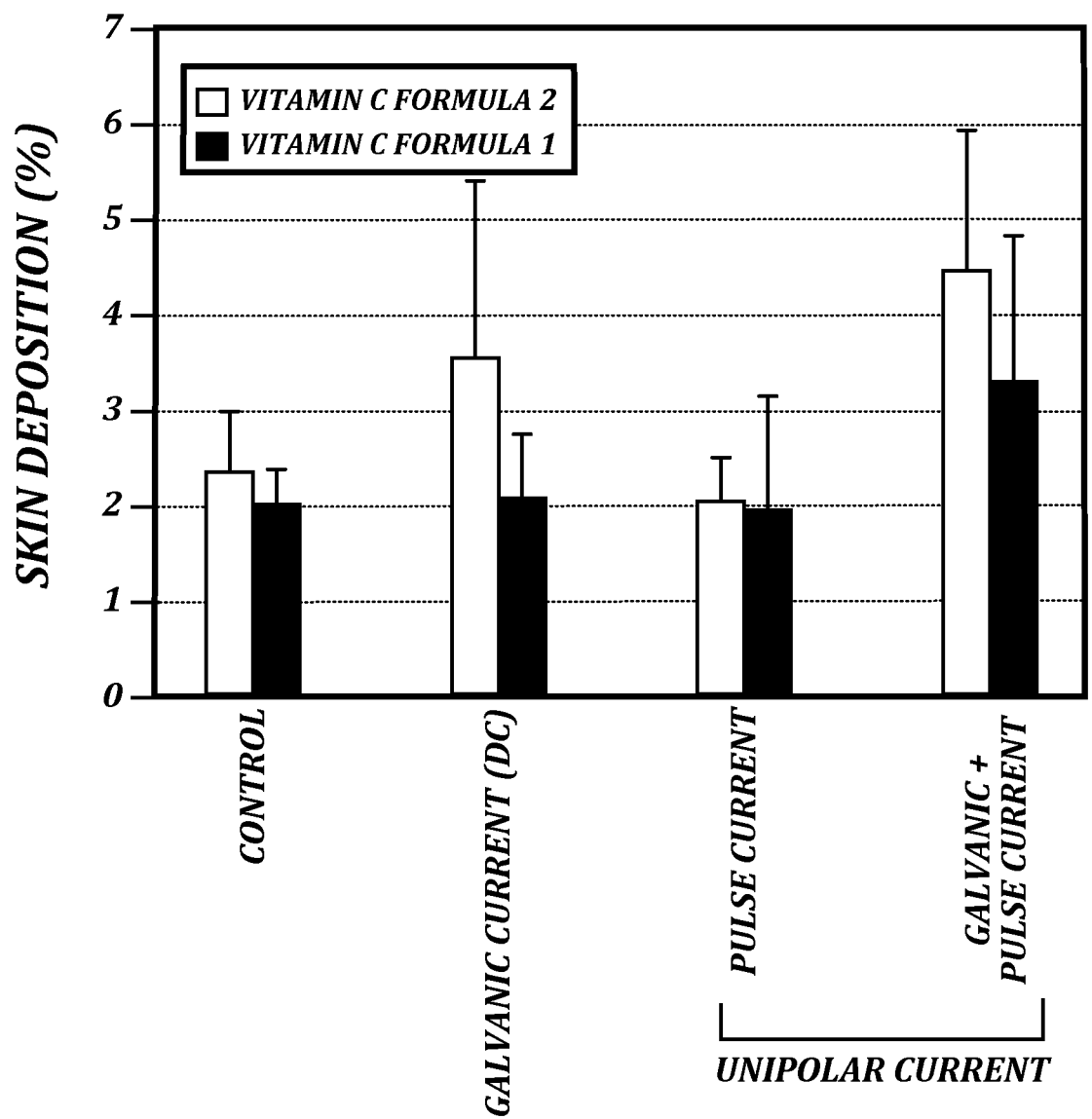
FIG. 5 is a graph comparing the efficacy of different electrical waveform stimuli for administration of vitamin C.

Three current profiles used a current density of 0.2 mA/cm$^2$: (i) galvanic (DC) (negative), (ii) square pulse current (negative, 2000 hertz, duty cycle 50%), and (iii) galvanic current (negative) coupled with pulse current (negative, 0.25 ms wide at −0.4 mA/cm$^2$ and 0.25 ms at 0 mA/cm$^2$) 200 Hz repetition. The control is topical application of the composition. The results are shown in FIG. 5.

The results show that iontophoresis using DC current and DC current in combination with pulse current resulted in greater deposition of vitamin C compared to the control for the composition containing 5% vitamin C. The deposition using DC current was 3.5% vitamin C and for DC current with pulse current, the deposition was 4.5% vitamin C. The results also show that iontophoresis using DC current in combination with pulse current resulted in greater deposition of vitamin C (about 3.3%) compared to the control for compositions containing 10% vitamin C.

Vitamin C demonstrates aqueous solubility, form ions, carries a negative charge in aqueous systems at a physiologically acceptable pH, and can be formulated at high concentration. In some embodiments, iontophoresis using DC current coupled with pulse current resulted in greater deposition over the control for the 5% and 10% vitamin C compositions.

The 10% vitamin C formula 1 and the 5% vitamin C formula 2 have complex compositions with many different excipients and were developed to facilitate passive administration of neutral (uncharged) ascorbic acid into the skin. The pKa of ascorbic acid in aqueous solution is =4.70. Given that pKa tends to increase in the presence of organic, non-aqueous solvents and formulations' pH of 6.7 and 6, respectively, it is likely that a considerable fraction of the ascorbic acid remains in a neutral state. Therefore, in the event that the ascorbic acid is not ionized, it cannot benefit from electromigration from the cathode upon application of a constant electric current. Indeed, unionized molecules are applied from the anode and use electroosmosis in order to improve their delivery by iontophoresis—their electrotransport will be hindered if they are applied from the cathode. In this case, assuming that ascorbic acid was present in its uncharged form in these formulations, which were iontophoresed at the cathode, it is possible that the results seen using profile (iii) were not due to electromigration but might be attributed to the effect of this current profile in increasing the passive permeability of the skin. Profile (iii) might function as a physical enhancement method to facilitate passive diffusion through a modified skin bather as is the case for electroporation.

While illustrative embodiments have been illustrated and described, it will be appreciated that various changes can be made therein without departing from the spirit and scope of the claimed subject matter.

The invention claimed is:

1. A iontophoresis method of delivering a cosmetic vitamin C composition through a skin, the iontophoresis method comprising:
    applying a selected current profile, a combination of a continuous direct current and a pulsed current, from any device and/or support comprising at least one electrode to a biological subject, the selected current profile of a potential, a current density and/or a frequency and for a duration sufficient to transdermally deliver vitamin C to the biological subject, the method also comprising the step of transporting different rates of vitamin C across the skin in accordance to the selected current profile,
    wherein applying the selected current profile to the biological subject includes concurrently delivering the continuous direct current and the pulsed current and generating the pulsed current with a stimulus having an average current density ranging from 0.005 mA/cm$^2$ to 0.5 mA/cm$^2$; a pulse duration ranging from 100 microseconds to 500 microseconds; and a pulse frequency ranging from 1 Hertz to 500 Hertz.

2. The iontophoresis method of claim 1, wherein applying the selected current profile to the biological subject includes generating a continuous direct current stimulus having an average current density ranging from 0.001 mA/cm$^2$ to 0.5 mA/cm$^2$.

3. The iontophoresis method of claim 1, wherein applying the selected current profile to the biological subject includes generating the pulsed current having sinusoidal waveforms, non-sinusoidal waveforms, or combinations thereof, or periodic square waveforms, rectangular waveforms, saw tooth waveforms, spiked waveforms, trapezoidal waveforms, triangle waveforms, or combinations thereof.

4. The iontophoresis method of claim 1, further comprising:
    transdermally delivering a composition including,
    one or more of vitamin C, vitamin C derivatives, ions of vitamin C, and ions of vitamin C derivatives present in amounts ranging from 0.01% to 100% by weight.

5. The iontophoresis method of the claim 4, further comprising:
    transdermally delivering an aqueous composition including,
    one or more silicon surface-active agents present in amounts ranging from 0.01% to 30% by weight;
    one or more ionic polymers present in amounts ranging from 0.01% to 10% by weight; and
    water present in an amount of at least 30% by weight.

6. The iontophoresis method of claim 1, further comprising:
    transdermally delivering an aqueous composition including,
    one or more of vitamin C, vitamin C derivatives, ions of vitamin C, and ions of vitamin C derivatives present in amounts ranging from 0.01% to 30% by weight;
    one or more silicon surface-active agents present in amounts ranging from 0.01% to 30% by weight;
    one or more non-ionic polymers present in amounts ranging from 0.01% to 20% by weight; and
    water present in an amount of at least 30% by weight.

7. The iontophoresis method of claim 1, wherein transdermally delivering vitamin C includes:
    generating a continuous direct current stimulus having an average current density ranging from 0.01 mA/cm$^2$ to 0.5 mA/cm$^2$; and generating a pulsed current stimulus having an average current density ranging from 0.01 mA/cm$^2$ to 10 mA/cm$^2$; a pulse duration ranging from 10 microseconds to 500 microseconds; and a pulse frequency ranging from 10 Hertz to 500 Hertz;

the continuous direct current and the pulsed current of a duration sufficient to transdermally deliver an aqueous active agent composition to a biological subject.

8. The iontophoresis method according to claim 1, comprising measuring at least one of temperature of the skin, impedance of the skin, and a pH of the cosmetic vitamin C composition.

* * * * *